United States Patent
Schafer et al.

(10) Patent No.: US 10,245,266 B2
(45) Date of Patent: Apr. 2, 2019

(54) 3-(4-((4-MORPHOLINOMETHYL-BENZYL)OXY)-1-OXOISOINDOLIN-2-YL)PIPERIDINE-2,6-DIONE FOR THE TREATMENT OF SYSTEMIC LUPUS ERYTHEMATOSUS

(71) Applicant: CELGENE CORPORATION, Summit, NJ (US)

(72) Inventors: Peter H. Schafer, Belle Mead, NJ (US); Lei Wu, Bridgewater, NJ (US); Ying Ye, Martinsville, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/312,450

(22) PCT Filed: May 18, 2015

(86) PCT No.: PCT/US2015/031345
§ 371 (c)(1),
(2) Date: Nov. 18, 2016

(87) PCT Pub. No.: WO2015/179276
PCT Pub. Date: Nov. 26, 2015

(65) Prior Publication Data
US 2017/0173029 A1 Jun. 22, 2017

Related U.S. Application Data

(60) Provisional application No. 62/053,626, filed on Sep. 22, 2014, provisional application No. 62/000,428, filed on May 19, 2014.

(51) Int. Cl.
*A61K 31/535* (2006.01)
*A61K 31/5377* (2006.01)
(Continued)

(52) U.S. Cl.
CPC ...... *A61K 31/5377* (2013.01); *A61K 31/5355* (2013.01); *G01N 33/6854* (2013.01);
(Continued)

(58) Field of Classification Search
CPC .......... A61K 31/5377; G01N 33/6854; G01N 33/6893; G01N 2800/24; G01N 2800/52
(Continued)

(56) References Cited

U.S. PATENT DOCUMENTS

| 5,635,517 A | 6/1997 | Muller et al. |
| 2008/0045485 A1 | 2/2008 | Mulr |

(Continued)

FOREIGN PATENT DOCUMENTS

| JP | 2008-263917 A | 6/2008 |
| WO | WO 99/47512 A1 | 9/1999 |

(Continued)

OTHER PUBLICATIONS

Nies et al., "Impaired Immunoglobulin Synthesis by Peripheral Blood Lymphocytes in Systemic Lupus Erythematosus", Arthritis and Rheumatism, 21(1):51-57 (1978).
(Continued)

*Primary Examiner* — Taylor V Oh
(74) *Attorney, Agent, or Firm* — Jones Day

(57) ABSTRACT

Provided herein are methods of using compounds and compositions for treating, managing, and/or preventing systemic lupus erythematosus (SLE). Pharmaceutical compositions and dosing regimens for use in the methods are also provided herein.

16 Claims, 10 Drawing Sheets

(51) Int. Cl.
*A61K 31/5355* (2006.01)
*G01N 33/68* (2006.01)

(52) U.S. Cl.
CPC ... *G01N 33/6893* (2013.01); *G01N 2800/104* (2013.01); *G01N 2800/24* (2013.01); *G01N 2800/52* (2013.01)

(58) Field of Classification Search
USPC ..................................................... 514/235.2
See application file for complete search history.

(56) References Cited

U.S. PATENT DOCUMENTS

| | | |
|---|---|---|
| 2011/0196150 A1 | 8/2011 | Man et al. |
| 2014/0045844 A1 | 2/2014 | Schafer et al. |
| 2014/0162282 A1 | 6/2014 | Schafer et al. |
| 2014/0343058 A1 | 11/2014 | Schafer et al. |
| 2015/0038511 A1 | 2/2015 | Schafer et al. |

FOREIGN PATENT DOCUMENTS

| | | |
|---|---|---|
| WO | WO 2003/018836 A2 | 3/2003 |
| WO | WO 2004/026844 A1 | 4/2004 |
| WO | WO 2007/133725 A1 | 11/2007 |
| WO | WO 2008/076356 A1 | 6/2008 |
| WO | WO 2008/115516 A2 | 9/2008 |
| WO | WO 2010/065865 A2 | 6/2010 |
| WO | WO 2011/100380 A1 | 8/2011 |
| WO | WO 2012/115885 A1 | 8/2012 |
| WO | WO 2014/004990 A2 | 1/2014 |
| WO | WO 2014/025958 A2 | 2/2014 |
| WO | WO 2015/054199 A1 | 4/2015 |
| WO | WO 2015/179276 A1 | 11/2015 |

OTHER PUBLICATIONS

Nilsson et al., "Purification and characterization of IgG immunoconglutinins from patients with systemic lupus erythematosus: implications for a regulatory function", Clin. exp. Immunol., 82:262-267 (1990).
Abud-Mendoza et al., "Treating severe systemic lupus erythematosus with rituximab. An open study," Reumatol. Clin., 5(4):147-152 (2009).
Anonymous: "Pomalidomide," Wikipedia, the free encyclopedia, Jul. 5, 2012, retrieved from the internet: URL:http://en.wikipedia.org/w/index.php?title=Pomalidomide&oldid=500784057, retrieved on Oct. 16, 2013 (2 pages).
Judson, "Extrapulmonary Sarcoidosis", Semin. Respir. Crit. Care Med., 28(1):83-101 (2007).
Khanna, "Diagnosis and treatment of systemic and localized scleroderma," Expert Rev. Dermatol., 6(3):287-302 (2011).
Kurzinski and Torok, "Cytokine profiles in localized scleroderma and relationship to clinical features," Cytokine, 55(2):157-164 (2011).
Risselada et al., "Therapy-resistent lupus skin disease successfully treated with rituximab", Rheumatology, 45:915-916 (2006).
Werth, "Current Treatment of Cutaneous Lupus Erythematosus", Dermatology Online Journal, 7(1):1-10 (2001).
Lee et al., "Disturbed Homeostasis and Multiple Signaling Defects in the Peripheral Blood B-Cell Compartment of Patients with Severe Chronic Sarcoidosis", Clin. Vaccine Immunol., 18(8):1306-1316 (2011).
Sweiss et al., "Rituximab in the treatment of refractory pulmonary sarcoidosis", Eur. Respir. J., 43:1525-1528 (2014).
Vyse et al. "Genetic Susceptibility to Systemic Lupus Erythematosus", Annu. Rev. Immunol. 16:261-292 (1998).
Buckley III et al., "A Comparison of Serum Immunoglobulin Concentrations in Sarcoidosis and Tuberculosis", Ann. Intern. Med. 72(1):37-42 (1970) (abstract only).

n = 3 donors

3-(4-((4-MORPHOLINOMETHYL-BENZYL)OXY)-1-OXOISOINDOLIN-2-YL) PIPERIDINE-2,6-DIONE FOR THE TREATMENT OF SYSTEMIC LUPUS ERYTHEMATOSUS

This application is a national phase entry pursuant to 35 U.S.C. § 371 of International Application No. PCT/US2015/031345, filed May 18, 2015, which claims priority to U.S. Provisional Application Nos. 62/000,428, filed May 19, 2014, and 62/053,626, filed Sep. 22, 2014, the entireties of which are incorporated herein by reference.

1. FIELD

Provided herein are methods of treating, preventing, and/or managing systemic lupus erythematosus (SLE), or one or more symptoms thereof, using Compound I or a pharmaceutically acceptable salt, solvate, hydrate, stereoisomer, tautomer or racemic mixtures thereof, including (S)-3-[4-(4-morphlin-4-ylmethylbenzyloxy)-1-oxo-1,3-dihydro-isoindo-2-yl]piperidine-2,6-dione. Pharmaceutical compositions and dosing regimens for such treatment, prevention, and/or management are also provided herein.

2. BACKGROUND

Systemic lupus erythematosus (SLE) is a multi-organ autoimmune disease of unknown etiology that has many clinical manifestations. Almost any organ can be involved, but the most common manifestations are cutaneous, musculoskeletal and renal. SLE typically affects young women of childbearing potential between the ages of 15 to 44. The prevalence of SLE is 300,000 patients in the United States and 4 million patients worldwide, with an annual incidence of 15,000 in the United States alone.

The pathogenesis of SLE likely involves an array of components associated with both genetic and environmental factors. Disease susceptibility is influenced by genes related to immune response and the major histocompatability complex class I and II genes. Additional susceptibilitystems from interactions between the hormonal environment and the hypothalamo-pituitaryadrenalaxis. In addition, the development of SLE is associated with a defective immuneresponse which affects apoptotic cell clearance and immune complexes. The loss of immunetolerance, excess T cell help, defective B cell suppression, and the shifting of T helper 1 (Th1) to Th2 and Th17 immune responses leads to B cell hyperactivity and the production of pathogenicantibodies. External factors such as chemicals, drugs, ultraviolet light, diet and viruses also contribute to the onset of disease.

As SLE is a waxing and waning disease, it is often controlled with NSAIDs or low potency immunosuppression drugs (antimalarials and low dose corticosteroids) for milder symptomology (muscoskeletal manifestation, cutaneous manifestation and serositis). More prolonged and potent use of corticosteroids, as well as non-biologic disease modifying anti-rheumatic drugs (DMARDs), are standard treatments which are also available to treat those patients who exhibit major organ involvement. In conjunction with standard therapy, biological DMARD therapies exist to augment treatment for those patients with more extensive disease. Belimumab, a monoclonal antibody and B-lymphocyte stimulator-specific inhibitor, has recently been approved for use in conjunction with corticosteroids and other standard therapies for autoantibody-positive SLE. In addition, Rituximab, a B-cell depleter, is often used off-label as rescue medication for patients unresponsive to standard treatment. However, there still remains a need for prophylactic or therapeutic drugs that can be used to treat or prevent SLE.

3. SUMMARY

Provided herein are methods of treating, managing, ameliorating and/or preventing systemic lupus erythematosus (SLE) comprising administering a therapeutically effective amount of a compound of formula I

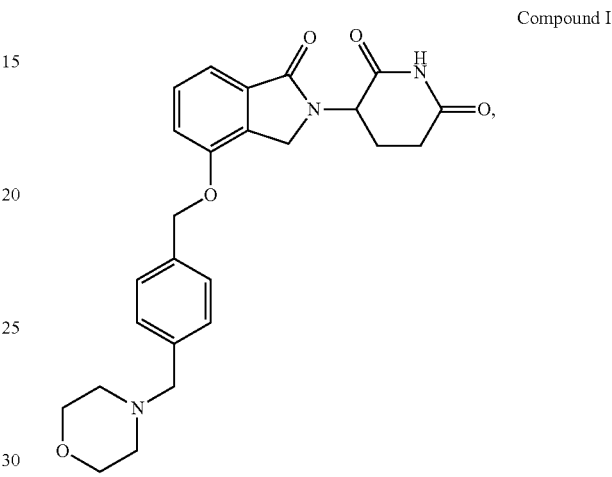

Compound I or a pharmaceutically acceptable salt, solvate, hydrate, stereoisomer, tautomer or racemic mixtures thereof.

In one embodiment, the compound is 3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of 3-[4-(4-morpholin-4-ylmethyl-benzyloxy)-1-oxo-1,3-dihydro-isoindol-2-yl]-piperidine-2,6-dione.

In one embodiment, the compound is 3-[4-(4-morpholin-4-ylmethyl-benzyloxy)-1-oxo-1,3-dihydro-isoindol-2-yl]-piperidine-2,6-dione hydrochloride.

In one embodiment, the compound is (S)-3-[4-(4-morpholin-4-ylmethyl-benzyloxy)-1-oxo-1,3-dihydro-isoindol-2-yl]-piperidine-2,6-dione, having the following structure:

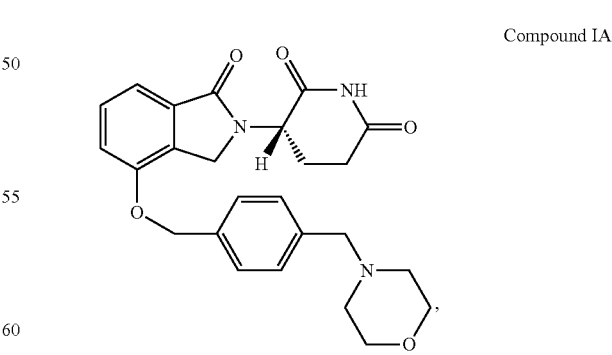

Compound IA or a pharmaceutically acceptable salt, solvate, hydrate, or tautomer thereof.

In one embodiment, the compound is (S)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (S)-3-[4-(4-morpholin-4-ylmethyl-benzyloxy)-1-oxo-1,3-dihydro-isoindol-2-yl]-piperidine-2,6-dione.

In one embodiment, the compound is (S)-3-[4-(4-morpholin-4-ylmethyl-benzyloxy)-1-oxo-1,3-dihydro-isoindol-2-yl]-piperidine-2,6-dione hydrochloride.

In one embodiment, the compound is (R)-3-[4-(4-morpholin-4-ylmethyl-benzyloxy)-1-oxo-1,3-dihydro-isoindol-2-yl]-piperidine-2,6-dione, having the following structure:

Compound IB

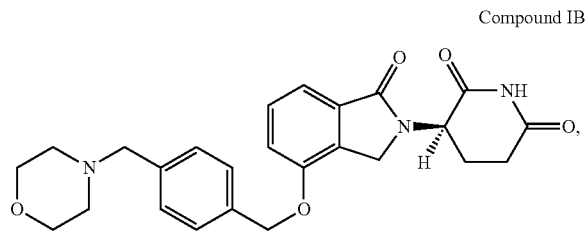 [SMILES: O=C1CC[C@@H](N2Cc3c(OCc4ccc(CN5CCOCC5)cc4)cccc3C2=O)C(=O)N1]

or a pharmaceutically acceptable salt, solvate, hydrate, or tautomer thereof.

In one embodiment, the compound is (R)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (R)-3-[4-(4-morpholin-4-ylmethyl-benzyloxy)-1-oxo-1,3-dihydro-isoindol-2-yl]-piperidine-2,6-dione.

In one embodiment, the compound is (R)-3-[4-(4-morpholin-4-ylmethyl-benzyloxy)-1-oxo-1,3-dihydro-isoindol-2-yl]-piperidine-2,6-dione hydrochloride.

In certain embodiments, one or more symptoms of SLE are treated, managed, and/or prevented.

Also provided herein are pharmaceutical compositions, single unit dosage forms, and kits suitable for use in treating, preventing, ameliorating and/or managing SLE, which comprise Compound I, or a pharmaceutically acceptable salt, solvate, hydrate, stereoisomer, tautomer or racemic mixtures thereof, optionally in combination with one or more other therapeutic agents.

Also provided herein are methods for identifying a subject having SLE who is likely to be responsive to a treatment with Compound I, or a pharmaceutically acceptable salt, solvate, hydrate, stereoisomer, tautomer or racemic mixture thereof.

Also provided herein are methods for assessing the efficacy of Compound I, or a pharmaceutically acceptable salt, solvate, hydrate, stereoisomer, tautomer or racemic mixture thereof, in treating, preventing or managing SLE.

4. BRIEF DESCRIPTION OF DRAWINGS

FIG. 1 is a schematic illustration of the overall clinical study design for Compound 1A in Systemic Lupus Erythematosus FIG. 2A, FIG. 2B, and FIG. 2C depict overexpression of CRBN, IKZF1 and IKZF3 mRNA in SLE peripheral blood mononuclear cells.

FIG. 3A, FIG. 3B, FIG. 3C, and FIG. 3D depict that Compound 1A reduced Aiolos and Ikaros protein levels in whole blood leukocyte subsets.

Figure 6A:
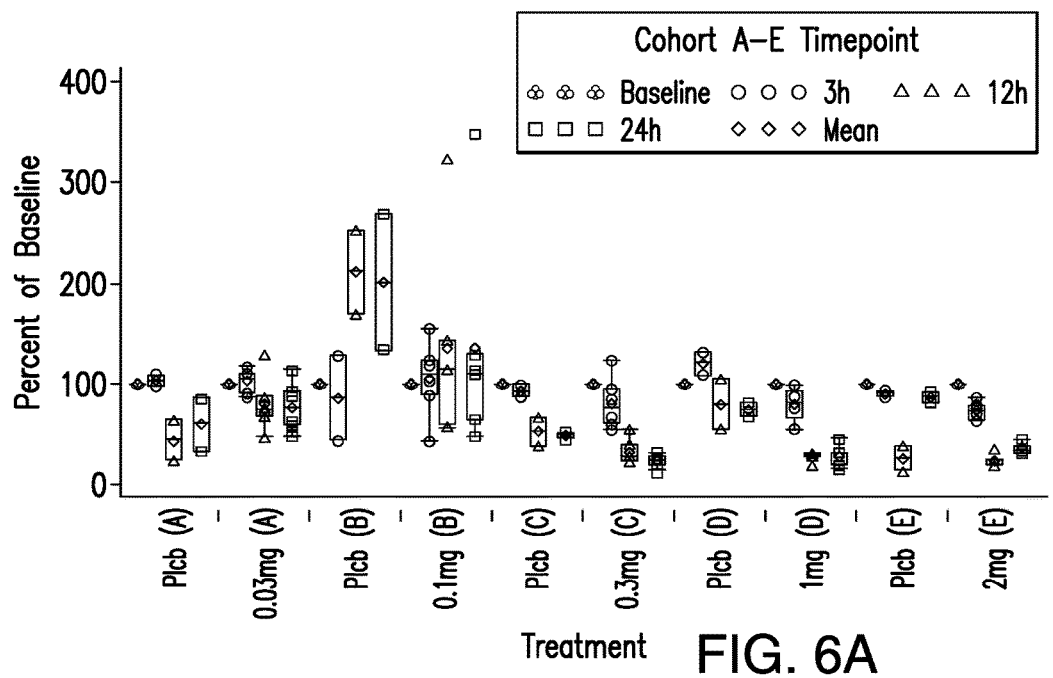
FIG. 6A depicts that Compound 1A reduces Aiolos expression in CD19+ B cells in healthy volunteers.
Figure 6B:
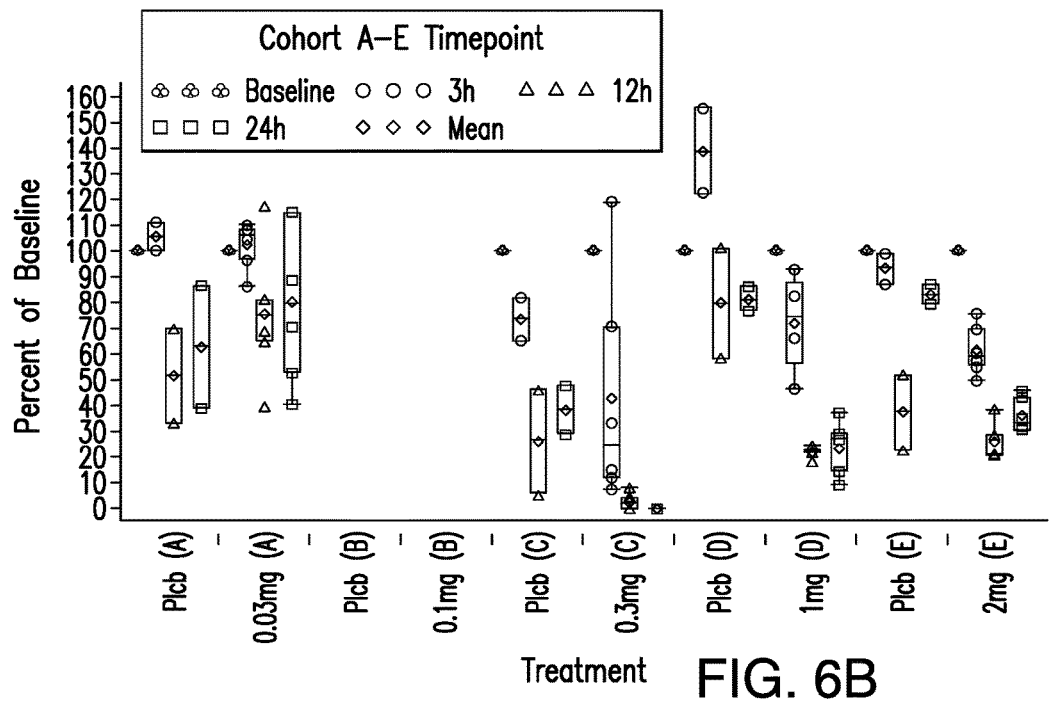

FIG. 6B depicted that Compound 1A reduced Aiolos expression in CD3+ T cells in healthy volunteers.

Figure 7A:
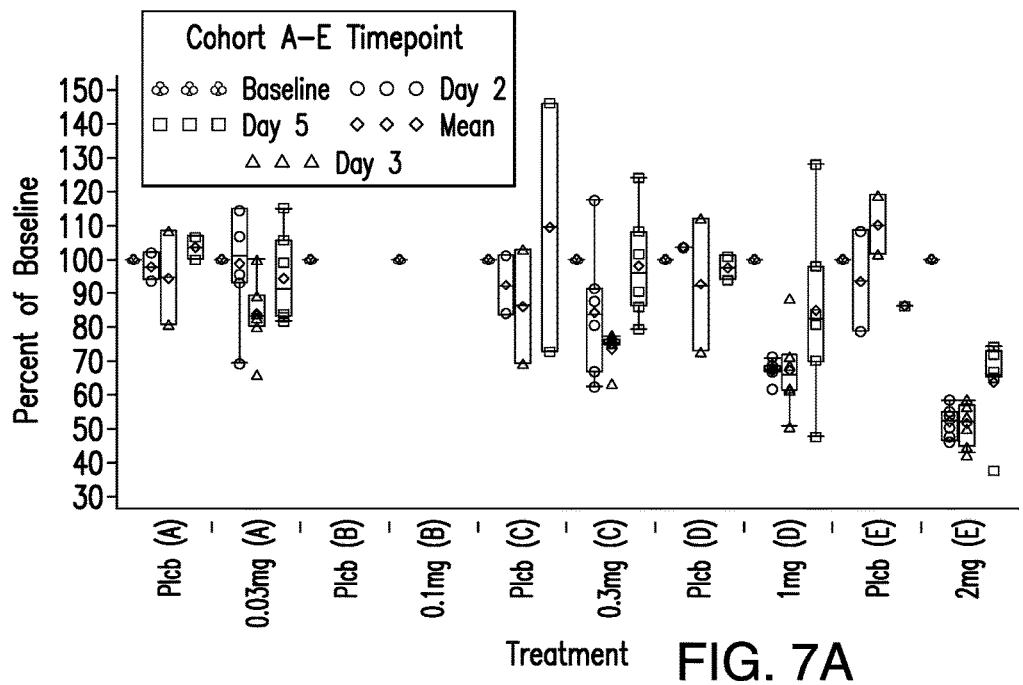

FIG. 7A depicts that Compound 1A reduces peripheral blood CD19+ B cell counts in healthy volunteers.

Figure 7B:
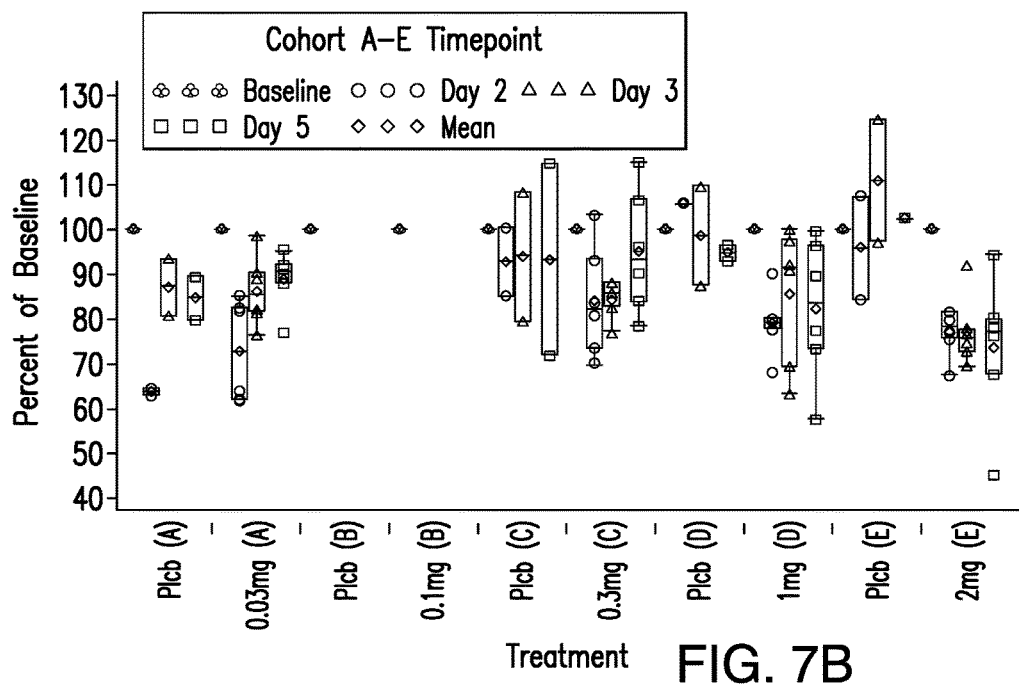

FIG. 7B depicts the effect of Compound 1A on peripheral blood CD3+ T cell counts in healthy volunteers.

Figure 8A:
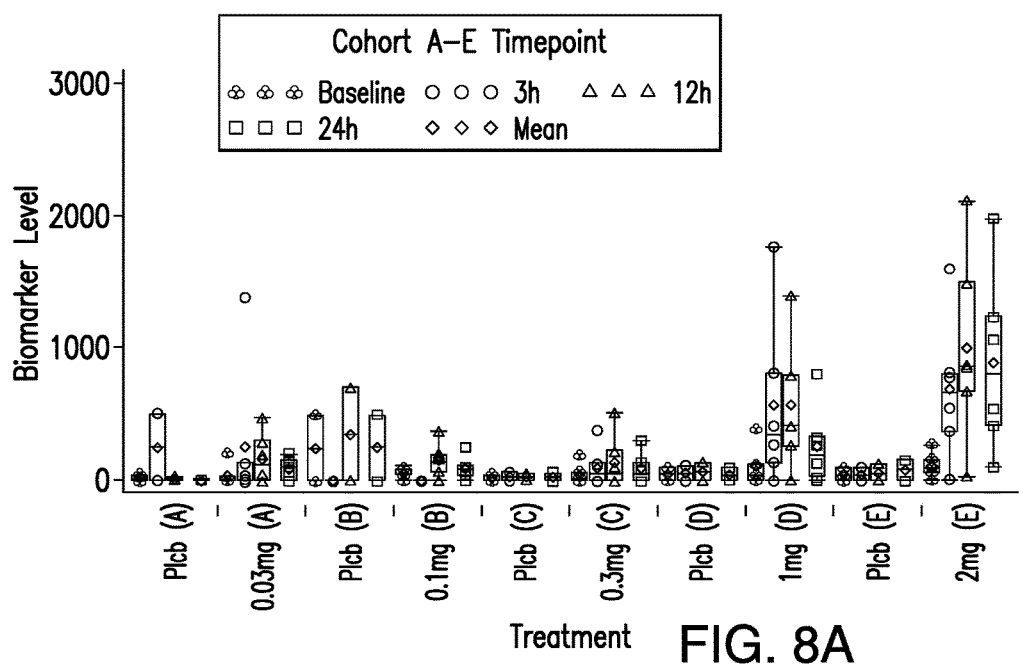

FIG. 8A depicts that Compound 1A dose-dependently increased IL-2 production in healthy volunteers.

Figure 8B:
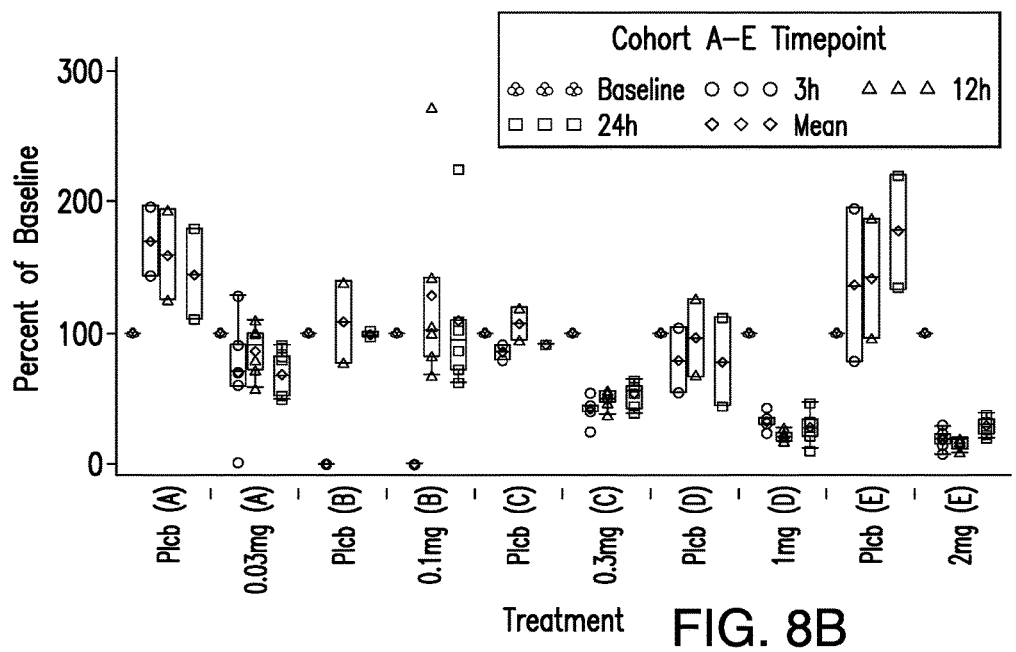

FIG. 8B depicts that Compound 1A dose-dependently decreased ex vivo IL-1β production in healthy volunteers.

5. DETAILED DESCRIPTION

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, and unless otherwise indicated, the terms "treat," "treating" and "treatment" refer to alleviating or reducing the severity of a disease or a symptom associated with the disease or condition being treated. The term contemplates that a compound provided herein is administered after the onset of a disease or a symptom associated with the disease or condition being treated.

As used herein, "prevent", "prevention" and other forms of the word include the inhibition of onset or progression of a disease or disorder or a symptom of the particular disease or disorder. In some embodiments, subjects with familial history of cancer are candidates for preventive regimens. Generally, in the context of cancer, the term "preventing" refers to administration of the drug prior to the onset of signs or symptoms of the disease being treated.

As used herein, and unless otherwise indicated, the term "managing" encompasses preventing the recurrence of the particular disease or disorder in a subject who had suffered from it, lengthening the time a subject who had suffered from the disease or disorder remains in remission, reducing mortality rates of the subjects, and/or maintaining a reduction in severity or avoidance of a symptom associated with the disease or condition being managed.

As used herein, the term "subject" or "patient" means an animal, typically a mammal, including a human being.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent.

As used herein, and unless otherwise specified, the term "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein and unless otherwise indicated, the term "pharmaceutically acceptable salt" includes, but is not limited to, a salt of an acidic group that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate.

As used herein and unless otherwise indicated, the term "hydrate" means a compound provided herein or a salt thereof, further including a stoichiometric or non-stoichiometric amount of water bound by non-covalent intermolecular forces. The hydrates can be crystalline or non-crystalline.

As used herein and unless otherwise indicated, the term "solvate" means a solvate formed from the association of one or more solvent molecules to compound provided herein. The term "solvate" includes hydrates (e.g., monohydrate, dihydrate, trihydrate, tetrahydrate, and the like). The solvates can be crystalline or non-crystalline.

As used herein, and unless otherwise specified, the term "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound provided herein is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds provided herein (e.g., R/S=30/70, 35/65, 40/60, 45/55, 55/45, 60/40, 65/35 and 70/30).

The terms "co-administration" and "in combination with" include the administration of two or more therapeutic agents (for example, Compound I or a composition provided herein and another modulator of leukocytic activity, including activity of B cells and/or T cells, monocytes, macrophages, and other lymphoid or myeloid-derived cell types or other active agent) either simultaneously, concurrently or sequentially with no specific time limits. In one embodiment, Compound I, or a pharmaceutically acceptable salt, solvate, hydrate, stereoisomer, tautomer or racemic mixtures thereof, and at least one other agent are present in the cell or in the subject's body at the same time or exert their biological or therapeutic effect at the same time. In one embodiment, the therapeutic agent(s) are in the same composition or unit dosage form. In another embodiment, the therapeutic agent (s) are in separate compositions or unit dosage forms.

5.1 Compound I

In certain embodiments, Compound I for use in the methods provided herein, including the combination therapy, and in compositions provided herein is a compound of formula:

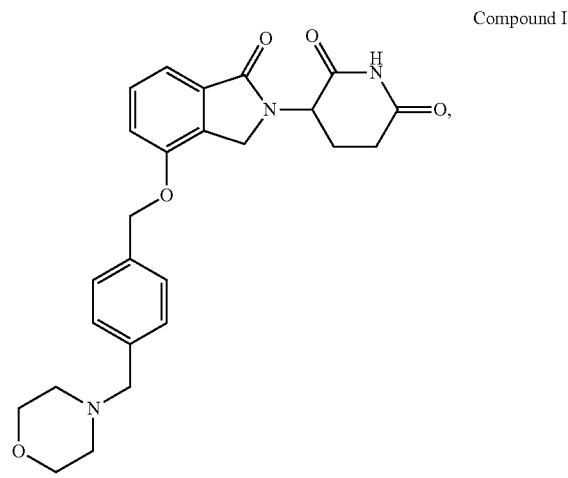 [SMILES: O=C1CCC(N2Cc3c(OCc4ccc(CN5CCOCC5)cc4)cccc3C2=O)C(=O)N1]

Compound I or a pharmaceutically acceptable salt, solvate, hydrate, stereoisomer, tautomer or racemic mixtures thereof.

In one embodiment, the compound is (S)-3-[4-(4-morpholin-4-ylmethyl-benzyloxy)-1-oxo-1,3-dihydro-isoindol-2-yl]-piperidine-2,6-dione, having the following structure:

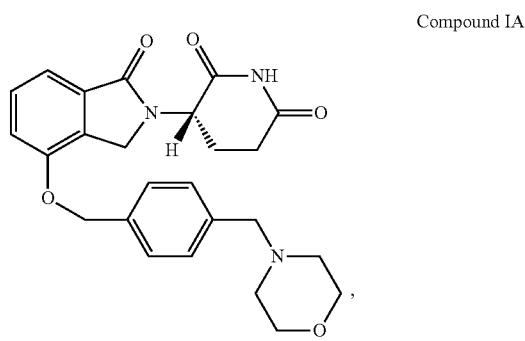 [SMILES: O=C1CC[C@H](N2Cc3c(OCc4ccc(CN5CCOCC5)cc4)cccc3C2=O)C(=O)N1]

Compound IA or a pharmaceutically acceptable salt, solvate, hydrate, or tautomer thereof.

In one embodiment, the compound is (S)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (S)-3-[4-(4-morpholin-4-ylmethyl-benzyloxy)-1-oxo-1,3-dihydro-isoindol-2-yl]-piperidine-2,6-dione.

In one embodiment, the compound is (S)-3-[4-(4-morpholin-4-ylmethyl-benzyloxy)-1-oxo-1,3-dihydro-isoindol-2-yl]-piperidine-2,6-dione hydrochloride.

In one embodiment, the compound is (R)-3-[4-(4-morpholin-4-ylmethyl-benzyloxy)-1-oxo-1,3-dihydro-isoindol-2-yl]-piperidine-2,6-dione, having the following structure:

Compound IB

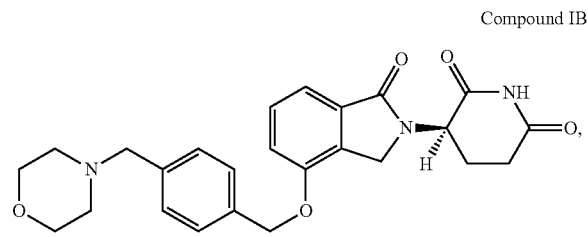 [SMILES: O=C1CC[C@@H](N2Cc3c(OCc4ccc(CN5CCOCC5)cc4)cccc3C2=O)C(=O)N1]

or a pharmaceutically acceptable salt, solvate, hydrate, or tautomer thereof.

In one embodiment, the compound is (R)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (R)-3-[4-(4-morpholin-4-ylmethyl-benzyloxy)-1-oxo-1,3-dihydro-isoindol-2-yl]-piperidine-2,6-dione.

In one embodiment, the compound is selected from 3-[4-(4-morpholin-4-ylmethyl-benzyloxy)-1-oxo-1,3-dihydro-isoindol-2-yl]-piperidine-2,6-dione, 3-[4-(4-morphlin-4-ylmethylbenzyloxy)-1-oxo-1,3-dihydro-isoindo-2-yl] piperidine-2,6-dione hydrochloride, (R)-3-[4-(4-morphlin-4-ylmethylbenzyloxy)-1-oxo-1,3-dihydro-isoindo-2-yl] piperidine-2,6-dione, (R)-3-[4-(4-morphlin-4-ylmethylbenzyloxy)-1-oxo-1,3-dihydro-isoindo-2-yl] piperidine-2,6-dione hydrochloride, (S)-3-[4-(4-morphlin-4-ylmethylbenzyloxy)-1-oxo-1,3-dihydro-isoindo-2-yl] piperidine-2,6-dione and (S)-3-[4-(4-morphlin-4-ylmethylbenzyloxy)-1-oxo-1,3-dihydro-isoindo-2-yl] piperidine-2,6-dione hydrochloride.

Compound I, or a pharmaceutically acceptable salt, solvate, hydrate, stereoisomer, tautomer or racemic mixtures thereof, can be prepared by methods known to one of skill in the art, for example, according to the procedure described in US Publication No. 2011/0196150, the entirety of which is incorporated herein by reference.

An exemplary method for preparation is described in Example 1.

5.2 Methods of Treatment

In certain embodiments, provided herein are methods of treating, preventing, and/or managing systemic lupus erythematosus (SLE), or a symptom thereof, comprising administering a therapeutically or prophylactically effective amount of Compound I, or a pharmaceutically acceptable salt, solvate, hydrate, stereoisomer, tautomer or racemic mixtures thereof, to a patient having SLE. In one embodiment, provided herein are methods of treating, preventing, and/or managing SLE or a symptom thereof, comprising administering a therapeutically effective amount of (S)-3-[4-(4-morphlin-4-ylmethylbenzyloxy)-1-oxo-1,3-dihydro-isoindo-2-yl]piperidine-2,6-dione, or a pharmaceutically acceptable salt or solvate thereof, to a patient having SLE.

In one embodiment, provided herein are methods of preventing SLE or a symptom thereof, comprising administering an effective amount of Compound I, or a pharmaceutically acceptable salt, solvate, hydrate, stereoisomer, tautomer or racemic mixtures thereof, to a patient at risk of having SLE. In one embodiment, provided herein are methods of preventing SLE or a symptom thereof, comprising administering an effective amount of (S)-3-[4-(4-morphlin-4-ylmethylbenzyloxy)-1-oxo-1,3-dihydro-isoindo-2-yl]piperidine-2,6-dione, or a pharmaceutically acceptable salt or solvate thereof, to a patient at risk of having SLE.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition). New York (US): McGraw-Hill; 2005. pp. 1960-1967).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash—a "butterfly" rash over the cheeks and bridge of the nose affects about half of people with SLE, in some patients, the rash gets worse in sunlight, and the rash may also be widespread.

Other symptoms depend on what part of the body is affected, and may include the following:

Brain and nervous system: headaches, numbness, tingling, seizures, vision problems, personality changes, Digestive tract: abdominal pain, nausea, and vomiting, Heart: abnormal heart rhythms (arrhythmias), Lung: coughing up blood and difficulty breathing, and Skin: patchy skin color, fingers that change color when cold (Raynaud's phenomenon).

In one embodiment, only skin symptoms are manifested in SLE, i.e., discoid lupus.

In one embodiment, SLE is skin predominant SLE.

In one embodiment, provided herein are methods of treating moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

Further provided herein are methods for achieving one or more clinical endpoints associated with SLE comprising administering an effective amount of Compound I, or a pharmaceutically acceptable salt, solvate, hydrate, stereoisomer, tautomer or racemic mixtures thereof, to a patient in need thereof.

Further provided herein are methods for increasing the overall survival, objective response rate, time to progression, progression-free survival and/or time-to-treatment failure of a patient having SLE comprising administering an effective amount of Compound I, or a pharmaceutically acceptable salt, solvate, hydrate, stereoisomer, tautomer or racemic mixtures thereof, to the patient.

The dose of Compound I, or a pharmaceutically acceptable salt, solvate, hydrate, stereoisomer, tautomer or racemic mixtures thereof, to be administered to a patient is rather widely variable and can be subject to the judgment of a health-care practitioner. Doses of Compound I, or a pharmaceutically acceptable salt, solvate, hydrate, stereoisomer, tautomer or racemic mixtures thereof, vary depending on factors such as: specific indication or symptoms to be treated, prevented, or managed; age and condition of a patient; and amount of second active agent used, if any. In general, Compound I, or a pharmaceutically acceptable salt, solvate, hydrate, stereoisomer, tautomer or racemic mixtures thereof, can be administered one to four or more times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight.

In one embodiment, one dose is given per day. In any given case, the amount of Compound I or a pharmaceutically acceptable salt, solvate, hydrate, stereoisomer, tautomer or racemic mixtures thereof administered will depend on such factors as the solubility of the active component, the formulation used and the route of administration. In one embodiment, application of a topical concentration provides intracellular exposures or concentrations of about 0.01-10 µM.

In certain embodiments, Compound I or a pharmaceutically acceptable salt, solvate, hydrate, stereoisomer, tautomer or racemic mixtures thereof is used in an amount of from about 0.1 mg to about 1000 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In other embodiments, the dose can be from about 0.1 mg to about 100 mg, from about 0.1 mg to about 50 mg, from about 0.1 mg to about 25 mg, from about 0.1 mg to about 20 mg, from about 0.1 mg to about 15 mg, from about 0.1 mg to about 10 mg, from about 0.1 mg to about 7.5 mg, from about 0.1 mg to about 5 mg, from about 0.1 mg to about 4 mg, from about 0.1 mg to about 3 mg, from about 0.1 mg to about 2 mg, or from about 1 mg to about 1 mg.

In some embodiments, Compound 1A, or a pharmaceutically acceptable salt or solvate thereof, is administered. In some embodiments, the dose of Compound 1A, or a pharmaceutically acceptable salt or solvate thereof, is from about 0.15 mg to about 0.6 per day. In one embodiment, the dose of Compound 1A, or a pharmaceutically acceptable salt or solvate thereof, is 0.3 mg given every other day. In one embodiment, the dose of Compound 1A, or a pharmaceutically acceptable salt or solvate thereof, is 0.3 mg given everyday. In one embodiment, the dose of Compound 1A, or a pharmaceutically acceptable salt or solvate thereof, is 0.6 mg and 0.3 mg given on alternating days. In one embodiment, the dose of Compound 1A, or a pharmaceutically acceptable salt or solvate thereof, is 0.6 mg given everyday.

In some embodiment, patients are started on high dose treatment, and if significant adverse effects persist, doses are adjusted, i.e., lowered, accordingly. For example, patients may start on a dose of 0.6 mg given everyday of Compound 1A, or a pharmaceutically acceptable salt or solvate thereon, and if significant adverse effects persist, then may adjust the dose in a step-wise fashion to 0.6 mg and 0.3 mg given on alternating days, then to 0.3 mg given everyday, and to 0.3 mg given every other day.

In some embodiments, administration of the compound continues for a period of from about 2 weeks to about 16 weeks. In one embodiment, administration of the compound continues for a period of about 28 days. In another embodiment, administration of the compound continues for a period of about 56 days. In yet another embodiment, administration of the compound continues for a period of about 84 days.

In some embodiments, the compound is administered orally. In one embodiment, the compound is administered in a capsule. In one embodiment, the capsule is in an amount of about 0.3 mg. In another embodiment, the compound is administered in a tablet.

In some embodiments, provided herein is a method for identifying a subject having systemic lupus erythematosus (SLE) who is likely to be responsive to a treatment with Compound I, or a pharmaceutically acceptable salt, solvate, hydrate, stereoisomer, tautomer or racemic mixture thereof, comprising:

(a) determining the level of a biomarker in a first sample from the subject, wherein the biomarker is selected from the group consisting of CRBN, IKZF1 (Ikaros), and IKZF3 (Aiolos); and (b) comparing the level of the biomarker in the first sample to a reference level of the biomarker; wherein the subject is likely to be responsive to the treatment if the level of the biomarker in the first sample is higher than the reference level of the biomarker.

In one embodiment, the method further comprises administering to the subject an effective amount of the compound.

In one embodiment, the reference is prepared by using a second sample obtained from a healthy subject not having SLE; and wherein the second sample is from the same source as the first sample.

In one embodiment, the biomarker is CRBN. In another embodiment, the biomarker is IKZF1. In yet another embodiment, the biomarker is IKZF3.

In one embodiment, the level of only one of the biomarkers is measured. In another embodiment, the levels of two or more of the biomarkers are monitored simultaneously.

In one embodiment, the first sample is peripheral blood mononuclear cells (PBMC). In another embodiment, the first sample is whole blood leukocyte. In one embodiment, the whole blood leukocyte is CD19+ B cells, CD3+ T cells, CD14+ monocytes, or granulocytes.

In one embodiment, the levels of one or more of the biomarkers are measured by determining the mRNA levels of the biomarkers. In another embodiment, the levels of one or more of the biomarkers are measured by determining the cDNA levels of the biomarkers. In yet another embodiment, the levels of one or more of the biomarkers are measured by determining the protein levels of the biomarkers.

In one embodiment, the compound is (S)-3-[4-(4-morph-lin-4-ylmethylbenzyloxy)-1-oxo-1,3-dihydro-isoindo-2-yl]piperidine-2,6-dione. In another embodiment, the compound is (S)-3-[4-(4-morphlin-4-ylmethylbenzyloxy)-1-oxo-1,3-dihydro-isoindo-2-yl]piperidine-2,6-dione hydrochloride.

In some embodiments, provided herein is a method of assessing the efficacy of Compound I, or a pharmaceutically acceptable salt, solvate, hydrate, stereoisomer, tautomer or racemic mixture thereof, in treating, preventing or managing systemic lupus erythematosus (SLE), comprising:

(a) administering the compound to a subject having SLE;
(b) obtaining a first sample from the subject;
(c) determining the level of a biomarker in the first sample; and
(d) comparing the level of the biomarker from step (c) to a reference level of the biomarker, wherein a change in the level as compared to the reference is indicative of the efficacy of the compound in treating SLE.

In one embodiment, the method further comprises adjusting the amount of the compound administered to the subject.

In one embodiment, the reference is prepared by using a second sample obtained from a healthy subject not having SLE; and wherein the second sample is from the same source as the first sample. In another embodiment, the reference is prepared by using a second sample obtained from the subject before administration of the compound; and wherein the second sample is from the same source as the first sample.

In one embodiment, the biomarker is CRBN. In another embodiment, the biomarker is IKZF1. In yet another embodiment, the biomarker is IKZF3. In yet another embodiment, the biomarker is an SLE autoantibody. In one embodiment, the SLE autoantibody is an anti-dsDNA autoantibody. In another embodiment, the SLE autoantibody is an anti-phospholipid autoantibody. In yet another embodiment, the biomarker is peripheral blood B cell count. In yet another embodiment, the biomarker is peripheral blood T cell count. In yet another embodiment, the biomarker is IL-1β. In yet another embodiment, the biomarker is IL-2.

In one embodiment, a decrease in the level of the biomarker in the first sample as compared to the reference is indicative of the efficacy of the compound in treating SLE. In another embodiment, an increase in the level of the biomarker in the first sample as compared to the reference is indicative of the efficacy of the compound in treating SLE.

In one embodiment, the level of only one of the biomarkers is measured. In another embodiment, the levels of two or more of the biomarkers are monitored simultaneously.

In one embodiment, the first sample is peripheral blood mononuclear cells (PBMC). In another embodiment, the first sample is whole blood leukocyte. In one embodiment, the whole blood leukocyte is CD19+ B cells, CD3+ T cells, CD14+ monocytes, or granulocytes.

In one embodiment, the levels of one or more of the biomarkers are measured by determining the mRNA levels of the biomarkers. In another embodiment, the levels of one or more of the biomarkers are measured by determining the cDNA levels of the biomarkers. In yet another embodiment, the levels of one or more of the biomarkers are measured by determining the protein levels of the biomarkers.

In one embodiment, the compound is (S)-3-[4-(4-morphlin-4-ylmethylbenzyloxy)-1-oxo-1,3-dihydro-isoindo-2-yl]piperidine-2,6-dione. In another embodiment, the compound is (S)-3-[4-(4-morphlin-4-ylmethylbenzyloxy)-1-oxo-1,3-dihydro-isoindo-2-yl]piperidine-2,6-dione hydrochloride.

5.3 Combination Therapy

Compound I, or a pharmaceutically acceptable salt, solvate, hydrate, stereoisomer, tautomer or racemic mixtures thereof, can be combined with other pharmacologically active compounds ("second active agents") in methods and compositions provided herein. Certain combinations may work synergistically in the treatment of SLE, and conditions and symptoms associated with SLE. Compound I, or a pharmaceutically acceptable salt, solvate, hydrate, stereoisomer, tautomer or racemic mixtures thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In another embodiment, the method of treatment provided herein comprises the administration of a second therapeutic agent, wherein the second therapeutic agent is an anti-inflammatory drug, e.g., a steroidal anti-inflammatory drug, or a non-steroidal anti-inflammatory drug (NSAID), acetaminophen, naproxen, ibuprofen, acetylsalicylic acid, and the like. In a more specific embodiment in which an NSAID is administered, a proton pump inhibitor (PPI), e.g., omeprazole may also administered. In one embodiment, the anti-inflammatory agent is a corticosteroid. In another embodiment, the antiinflammatory agent is colchicine.

In another embodiment, the second therapeutic agent is an immunomodulatory compound or an immunosuppressant compound such as azathioprine (Imuran™, Azasan™), methotrexate (Rheumatrex™, Trexall™), penicillamine (Depen™, Cuprimine™), cyclophosphamide (Cytoxan™), mycophenalate (CellCept™, Myfortic™), bosentan (Tracleer®), prednisone (Deltasone™, Liquid Pred™), and a PDE5 inhibitor. In another embodiment, where the affected individual has digital ulcerations and pulmonary hypertension, a vasodilator such as prostacyclin (iloprost) may be administered.

In another embodiment, the second therapeutic agent is an HDAC inhibitor, such as romidepsin, vorinostat, panobinostat, valproic acid, or belinostat; or a biological agent, such as an interleukin, an immunomodulatory monoclonal antibody, or *bacillus* Calmette-Guérin (BCG).

In another embodiment, the second therapeutic agent is an inhibitor of ActRII receptors or an activin-ActRII inhibitor. Inhibitors of ActRII receptors include ActRIIA inhibitors and ActRIIB inhibitors Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker.

Examples of non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

In one embodiment, the inhibitor of ActRII receptors is ACE-11. In another embodiment, the inhibitor of ActRII receptors is ACE-536.

In another embodiment, the second therapeutic agent is an agent that is conventionally used to treat SLE. Examples of such agents include, but are not limited to, an NSAID, a corticosteroid, a non-biologic disease modifying anti-rheumatic drug (DMARD), and a biological DMARD therapy (e.g., belimumab and rituximab).

Any combination of the above therapeutic agents, suitable for treatment of SLE or symptoms thereof, can be administered. Such therapeutic agents can be administered in any combination with Compound I, or a pharmaceutically acceptable salt, solvate, hydrate, stereoisomer, tautomer or racemic mixtures thereof, at the same time or as a separate course of treatment.

5.4 Cycling Therapy

In certain embodiments, Compound I, or a pharmaceutically acceptable salt, solvate, hydrate, stereoisomer, tautomer or racemic mixtures thereof, is cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.03 mg to about 10 mg per day, followed by a rest of one or two weeks. In other embodiments, the dose can be from about 0.1 mg to about 8 mg, from about 0.3 mg to about 6 mg, from about 1 mg to about 4 mg, or about 2 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

5.5 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, hydrate, stereoisomer, racemate, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences*, $20^{th}$ ed., Mack Publishing, Easton Pa. (2000).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

5.5.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

5.5.2 Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

5.5.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

5.5.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, $16^{th}$, $18^{th}$ and $20^{th}$ eds., Mack Publishing, Easton Pa. (1980, 1990 and 2000); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences*, $16^{th}$, $18^{th}$ and $20^{th}$ eds., Mack Publishing, Easton Pa. (1980, 1990 and 2000).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, hydrates, prodrugs, clathrates, or stereoisomers of the active ingredients can be used to further adjust the properties of the resulting composition.

5.5.5 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as other anti-inflammatory, immunomodulatory or immunosuppressant compounds, or a combination thereof. Examples of the additional active ingredients include, but are not limited to, those disclosed herein.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

The following Examples are presented by way of illustration, not limitation. In the examples, test compound refers to (S)-3-[4-(4-morphlin-4-ylmethylbenzyloxy)-1-oxo-1,3-dihydro-isoindo-2-yl]piperidine-2,6-dione.

6.1 Example 1: Preparation of (S)-3-[4-(4-morphlin-4-ylmethylbenzyloxy)-1-oxo-1,3-dihydro-isoindo-2-yl]piperidine-2,6-dione hydrochloride

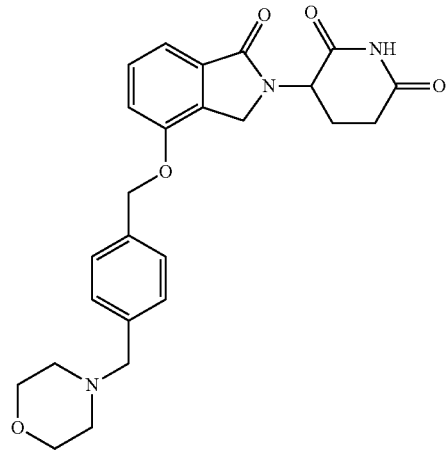 [SMILES: O=C1CCC(N2Cc3c(OCc4ccc(CN5CCOCC5)cc4)cccc3C2=O)C(=O)N1]

6.1.1 3-Hydroxy-2-methyl-benzoic acid methyl ester

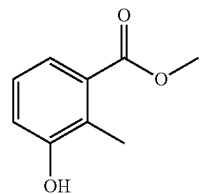

3-Hydroxy-2-methylbenzoic acid (105 g, 690 mmol) was added to MeOH (800 mL) in a 2 L three neck round bottom flask equipped with condenser, thermometer and stirring bar followed by the addition of MeOH (250 ml). $H_2SO_4$ (10 mL, 180 mmol) was added to above solution. The reaction mixture was stirred at 62° C. for 17 hours. The solvent was removed in vacuo. The residue (200 mL) was added to water (600 mL) slowly at room temperature and a white solid was formed. The suspension was stirred in an ice bath for 30 minutes and filtered. The solid was washed with water (5×250 mL) and dried to give 3-hydroxy-2-methyl-benzoic acid methyl ester as a white solid (100 g, 87% yield). The compound was used in the next step without further purification: LCMS MH=167; $^1$H NMR (DMSO-$d_6$) δ 2.28 (s, 3H, $CH_3$), 3.80 (s, 3H, $CH_3$), 6.96-7.03 (m, 1H, Ar), 7.09 (t, J=7.8 Hz, 1H, Ar), 7.14-7.24 (m, 1H, Ar), 9.71 (s, 1H, OH).

6.1.2 3-(tert-Butyl-dimethyl-silanyloxy)-2-methyl-benzoic acid methyl ester

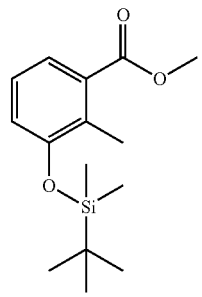 [SMILES: COC(=O)c1cccc(O[Si](C)(C)C(C)(C)C)c1C]

To a 1 L three neck RB flask equipped with stirring bar and thermometer, were added DMF (300 mL), methyl 3-hydroxy-2-methylbenzoate (90 g, 542 mmol) and imidazole (92 g, 1,354 mmol). TBDMS-Cl (90 g, 596 mmol) was added to the above solution in portions to control the internal temp between 15-19° C. over 20 minutes, and after addition, the internal temp dropped below 1° C. The ice bath was removed and the reaction mixture was stirred at room temperature for 16 hours. The reaction mixture was added to ice water (500 mL), and the resulting solution was divided into two portions (700 mL×2). Each portion was extracted with EtOAc (700 mL). Each organic layer was washed with cold water (350 mL) and brine (350 mL). Organic layers were combined and dried by $MgSO_4$. The combined organic layer was concentrated to give 3-(tert-butyl-dimethyl-silanyloxy)-2-methyl-benzoic acid methyl ester as a light brown oil (160 g, 100% crude yield). The compound was used in the next step without further purification: LCMS MH=281; $^1$H NMR (DMSO-$d_6$) δ −0.21 (s, 6H, $CH_3$, $CH_3$), 0.73-0.84 (m, 9H, $CH_3$, $CH_3$, $CH_3$), 2.10 (s, 3H, $CH_3$), 3.60 (s, 3H, $CH_3$), 6.82 (dd, 1H, Ar), 6.97 (t, J=7.9 Hz, 1H, Ar), 7.13 (dd, J=1.1, 7.7 Hz, 1H, Ar).

6.1.3 2-Bromomethyl-3-(tert-butyl-dimethyl-silanyloxy)-benzoic acid methyl ester

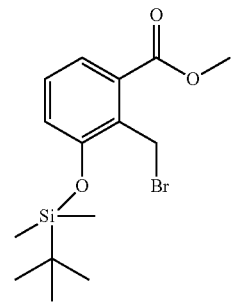 [SMILES: COC(=O)c1cccc(O[Si](C)(C)C(C)(C)C)c1CBr]

NBS (49.8 g, 280 mmol) was added to methyl 3-(tert-butyl dimethylsilyloxy)-2-methylbenzoate (78.4 g, 280 mmol) in methyl acetate (500 mL) at room temperature to give an orange colored suspension. The resulting reaction mixture was heated in an oil bath at 40° C. and shined by 300 wt sunlight bulb at reflux for 4 hours. The reaction mixture was cooled down and washed by $Na_2SO_3$ solution (2×600 mL, 50% saturated concentration), water (500 mL) and brine (600 mL). The organic layer was dried by $MgSO_4$ and decolorized by charcoal. The organic layer was concentrated to give 2-bromomethyl-3-(tert-butyl-dimethyl-silanyloxy)-benzoic acid methyl ester as a light brown oil (96 g, 91% crude yield). The compound was used in the next step without further purification: LCMS M-Br=279; $^1$H NMR (DMSO-$d_6$) δ 0.05-0.11 (m, 6H, $CH_3$, $CH_3$), 0.82 (s, 9H, $CH_3$, $CH_3$, $CH_3$), 3.65 (s, 3H, $CH_3$), 4.74 (s, 2H, $CH_2$), 6.94 (dd, J=1.3, 8.1 Hz, 1H, Ar), 7.10-7.20 (m, 1H, Ar), 7.21-7.29 (m, 1H, Ar).

6.1.4 4-Carbamoyl-butyric acid methyl ester

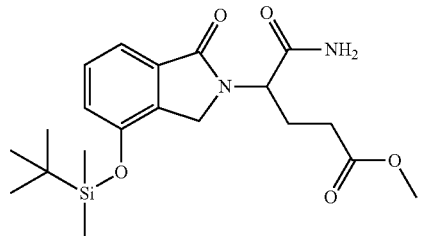 [SMILES: COC(=O)CCC(C(N)=O)N1Cc2c(O[Si](C)(C)C(C)(C)C)cccc2C1=O]

To a stirred solution of methyl 2-(bromomethyl)-3-(tert-butyldimethylsilyloxy)benzoate (137.5 g, 325 mmol) in acetonitrile (1100 mL) in a 2 L round bottom flask, was added methyl 4,5-diamino-5-oxopentanoate hydrochloride (70.4 g, 358 mmol). To the suspension was added DIPEA (119 ml, 683 mmol) through an addition funnel over 10 minutes and the suspension was stirred at room temperature for 1 hour before the mixture was heated in an oil bath at 40° C. for 23 hours. The reaction mixture was concentrated under vacuo. The residue was stirred in ether (600 mL), and a white solid precipitated out. The mixture was filtered and the solid was washed with ether (400 mL). The filtrate was washed with HCl (1N, 200 mL), $NaHCO_3$ (sat. 200 mL) and brine (250 mL). The aqueous acid layer and basic layer were kept separately. Then the solid was further washed with ether (250 mL) and the liquid was washed with above acid solution and basic solution. The two organic layers were combined and concentrated under vacuo to give 4-[4-(tert-Butyl-dimethyl-silanyloxy)-1-oxo-1,3-dihydro-isoindol-2-yl]-4-carbamoyl-butyric acid methyl ester as a brown oil (152 g, 115% crude yield, 77% purity by H NMR). The compound was used in the next step without further purification: LCMS MH=407.

6.1.5 4-Carbamoyl-4-(4-hydroxy-1-oxo-1,3-dihydro-isoindol-2-yl)-butyric acid methyl ester

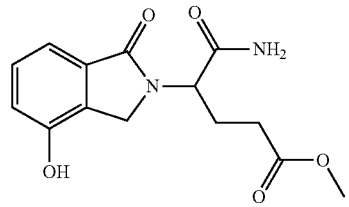 [SMILES: COC(=O)CCC(C(N)=O)N1Cc2c(O)cccc2C1=O]

To a stirred cold solution of methyl 5-amino-4-(4-(tert-butyldimethylsilyloxy)-1-oxoisoindolin-2-yl)-5-oxopentanoate (152 g, 288 mmol) in DMF (500 mL) and water (55 mL), was added by $K_2CO_3$ (19.89 g, 144 mmol) by portions over 5 minutes. The resulting reaction mixture was stirred at room temperature for 40 minutes. The reaction mixture was cooled in an ice bath. To the mixture, HCl (12M, 23.99 ml, 288 mmol) was added slowly. After the addition, acetonitrile (280 mL) was added to the mixture and a solid precipitated out. The mixture was stirred at room temperature for 10 minutes and filtered. The solid was washed with acetonitrile (50 mL×4). The filtrate was concentrated under high vacuo to give a yellow oil (168 g). The oil was dissolved in acetonitrile (600 mL) and stirred at room temperature for 10 minutes. The mixture was filtered and the solid was washed with acetonitrile (25 mL×2). The filtrate was concentrated under high vacuo to give a yellow oil (169 g), which was added to a mixture of water (1200 mL) and ether (1000 mL). The mixture was stirred for 3 minutes and the layers were separated. The aqueous solution was concentrated under high vacuo and the residue was stirred in acetonitrile (160 mL) and a white solid was formed after overnight stirring. The mixture was filtered to give 4-carbamoyl-4-(4-hydroxy-1-oxo-1,3-dihydro-isoindol-2-yl)-butyric acid methyl ester as a white solid (46 g, 54% yield). The filtrate was concentrated and the residue was further crystallized in acetonitrile (60 mL) to give more 4-carbamoyl-4-(4-hydroxy-1-oxo-1,3-dihydro-isoindol-2-yl)-butyric acid methyl ester as a white solid (11.7 g, 14% yield). The filtrate was concentrated and the residue was purified by ISCO chromatography to give more 4-carbamoyl-4-(4-hydroxy-1-oxo-1,3-dihydro-isoindol-2-yl)-butyric acid methyl ester as a white solid (13.2 g, 15% yield). The total product obtained was 70.9 g in 83% yield: LCMS MH=293; $^1$H NMR (DMSO-$d_6$) δ 1.95-2.34 (m, 4H, $CH_2$, $CH_2$), 3.51 (s, 3H, $CH_3$), 4.32 (d, J=17.6 Hz, 1H, CHH), 4.49 (d, J=17.4 Hz, 1H, CHH), 4.73 (dd, J=4.7, 10.2 Hz, 1H, CHH), 6.99 (dd, J=0.8, 7.9 Hz, 1H, Ar), 7.10-7.23 (m, 2H, Ar, NHH), 7.25-7.38 (m, 1H, Ar), 7.58 (s, 1H, NHH), 10.04 (s, 1H, OH).

6.1.6 3-(4-((4-(morpholinomethyl)benzyl)oxy)-1-oxoisoindolin-2-yl)piperidine-2,6-dione

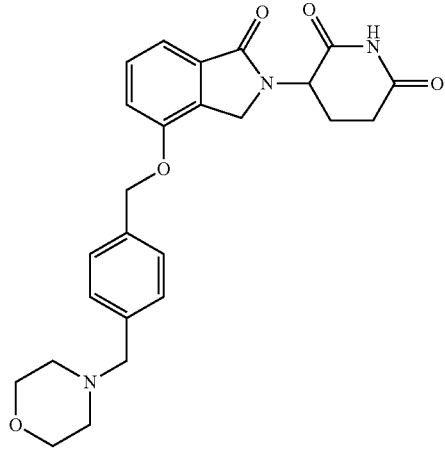 [SMILES: O=C1CCC(N2Cc3c(OCc4ccc(CN5CCOCC5)cc4)cccc3C2=O)C(=O)N1]

Step 1: To the solution of 3-(4-hydroxy-1-oxo-1,3-dihydro-isoindol-2-yl)-piperidine-2,6-dione (2.5 g, 8.56 mmol) in THF (60 mL) was added triphenyl phosphine (polymer supported 1.6 mmol/g, 12 g, 18.8 mmol). The mixture was stirred at room temperature for 15 minutes. Diisopropyl azodicarboxylate (3.96 mL, 18.8 mmol) was added at 0° C., and the mixture was stirred at 0° C. for 30 minutes. (4-Morpholin-4-ylmethyl-phenyl)-methanol (2.62 g, 12.4 mmol) was added at 0° C., and the mixture was allowed to warm to room temperature and stirred at room temperature overnight. The reaction mixture was filtered, and the filtrate was concentrated. The resulting oil was purified on silica gel column eluted with methylene chloride and methanol (gradient, product came out at 6% methanol) to give 4-carbamoyl-4-[4-(4-morpholin-4-ylmethyl-benzyloxy)-1-oxo-1,3-dihydro-isoindol-2-yl]-butyric acid methyl ester (2.2 g, 54% yield). The product was used in the next step without further purification.

Step 2: To the THF solution (50 mL) of 4-carbamoyl-4-[4-(4-morpholin-4-ylmethyl-benzyloxy)-1-oxo-1,3-dihydro-isoindol-2-yl]-butyric acid methyl ester (2.2 g, 4.57 mmol) was added potassium tert-butoxide (0.51 g, 4.57 mmol) at 0° C. The mixture was stirred at 0° C. for 10 minutes and was quenched with 1N HCl (5 mL, 5 mmol) followed by saturated $NaHCO_3$ (25 mL). The mixture was extracted with EtOAc (2×50 mL). The organic layer was washed with water (30 mL), brine (30 mL), dried over $MgSO_4$ and concentrated. To the resulting solid was added EtOAc (10 mL) followed by hexane (10 mL) under stirring. The suspension was filtered to give 3-(4-((4-(morpholinomethyl)benzyl)oxy)-1-oxoisoindolin-2-yl)piperidine-2,6-dione as white solid (1.5 g, 73% yield). HPLC: Waters Symmetry $C_{18}$, 5 μm, 3.9×150 mm, 1 mL/min, 240 nm, gradient to 95/5 acetonitrile/0.1% $H_3PO_4$ in 5 min: $t_R$=4.78 min (97.5%); mp: 210-212° C.; $^1$H NMR (DMSO-$d_6$) δ 1.86-2.09 (m, 1H, CHH), 2.29-2.38 (m, 4H, $CH_2$, $CH_2$), 2.44 (dd, J=4.3, 13.0 Hz, 1H, CHH), 2.53-2.64 (m, 1H, CHH), 2.82-2.99 (m, 1H, CHH), 3.46 (s, 2H, $CH_2$), 3.52-3.61 (m, 4H, $CH_2$, $CH_2$), 4.18-4.51 (m, 2H, $CH_2$), 5.11 (dd, J=5.0, 13.3 Hz, 1H, NCH), 5.22 (s, 2H, $CH_2$), 7.27-7.38 (m, 5H, Ar), 7.40-7.53 (m, 3H, Ar), 10.98 (s, 1H, NH) $^{13}$C NMR (DMSO-$d_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for $C_{25}H_{27}N_3O_5$+0.86 $H_2O$: C, 64.58; H, 6.23; N, 9.04; Found: C, 64.77; H, 6.24; N, 8.88.

(S)-3-(4-((4-(morpholinomethyl)benzyl)oxy)-1-oxoisoindolin-2-yl)piperidine-2,6-dione and (R)-3-(4-((4-(morpholinomethyl)benzyl)oxy)-1-oxoisoindolin-2-yl)piperidine-2,6-dione were prepared from 3-(4-((4-(morpholinomethyl)benzyl)oxy)-1-oxoisoindolin-2-yl)piperidine-2,6-dione through chiral separation.

6.2 Example 2: Clinical Studies—SLE

6.2.1 Study Design

A phase 2, randomized, placebo-controlled, double-blind, pilot, multicenter study is conducted to evaluate the preliminary efficacy, safety, tolerability, pharmacokinetics, pharmacodynamics and pharmacogenetics of Compound 1 in subjects with SLE. This study is conducted in two parts.

Part 1

Figure 1:
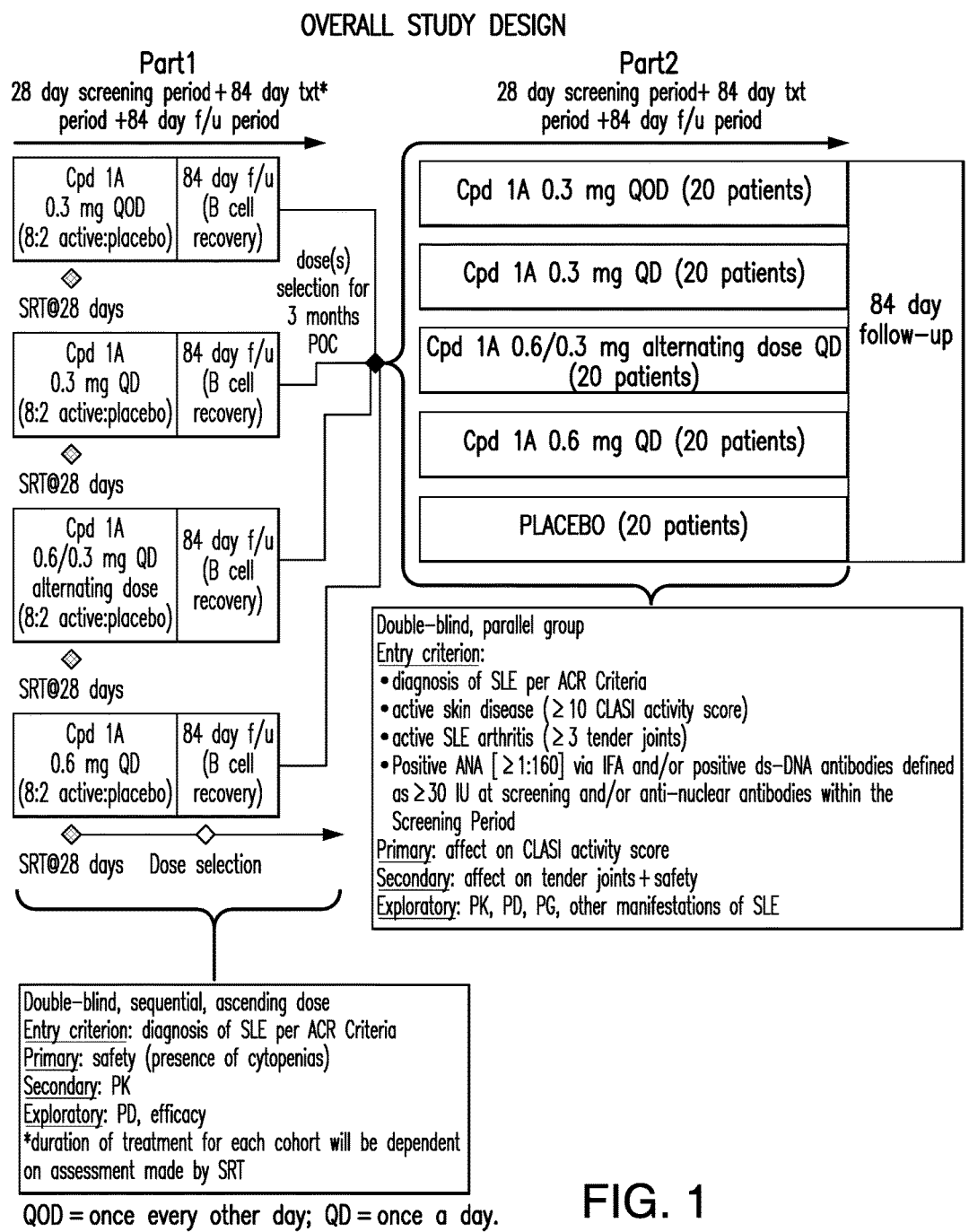

Part 1 is a randomized, double-blind, placebo-controlled, ascending dose study to evaluate the safety and tolerability of Compound 1A in SLE subjects. Subject participation in Part 1 will consist of 3 phases:

Pre-treatment Screening Phase: up to 28 days prior to the first dose of the investigational product (IP)
Treatment Phase: Up to 84 days
Observation Phase: 84 day post-treatment A total of approximately 40 subjects will be randomized into 4 dose groups with a 4:1 ratio of Compound 1A (0.3 mg every other day [QOD], 0.3 mg everyday [QD], 0.6 mg and 0.3 mg on alternating days and 0.6 mg QD) or matching placebo (8 subjects in the IP arm and 2 subjects in the placebo arm for each dose group) using an Interactive Voice Response System (IVRS). Subjects will be randomized into the first two dose groups of 0.3 mg QOD and 0.3 mg QD in parallel. Following confirmation of safety of the first two dose groups, remaining subjects will then be randomized into the 0.6 mg and 0.3 mg on alternating days and 0.6 mg QD dose groups in a sequential, dose-ascending manner (first the 0.6 mg and 0.3 mg on alternating days dose group followed by the 0.6 mg QD dose group). The treatment phase will be up to 84 days in duration for all dose groups. Subjects who discontinue IP early will enter into the observational follow-up phase for an 84 day period. In all cases of Early Termination from the study, subjects will be encouraged to complete an Early Termination Visit. A graphical representation of Part 1 dosing administration schedule is shown in FIG. 1.

All subjects will be allowed to remain on stable doses of hydroxychloroquine, chloroquine, and/or quinacrine during the course of the study, provided subjects are on one of these antimalarials for ≥16 weeks prior to their baseline visit and maintain a stable dose for at least 4 weeks prior to dosing and throughout the study. No additional systemic immunosuppressives will be permitted. In addition, as needed (PRN) treatment with systemic anti-pruritics and/or systemic analgesics will be permitted, however, subjects must stop using all systemic anti-pruritics 48 hours prior to all study visits and systemic analgesics 12 hours prior to all study visits. Oral non-steroidal anti-inflammatory drugs (NSAIDs) may be used PRN, but must be stopped 12 hours prior to all study visits. Use of oral corticosteroids will be permitted only at doses of 10 mg or less per day and must be maintained at a stable dose during study participation. No IV corticosteroids will be permitted during the study. No other, local or systemic treatments for dermatological manifestations of lupus will be permitted.

Following completion of the first 28 days of the treatment phase by at least 8 subjects in Dose Group 1 (0.3 mg QOD) and Dose Group 2 (0.3 QD), an assessment of safety and tolerability will be conducted. If Dose Group 1 and 2 are deemed safe, subjects will continue to receive study medication for up to 84 days and enrollment of subjects into Dose Group 3 (0.6 mg and 0.3 mg on alternating days) will be initiated. Following completion of the first 28 days of the treatment phase by at least 8 subjects in Dose Group 3 (0.6 mg and 0.3 mg on alternating days), an assessment of safety and tolerability will be conducted. If Dose Group 3 is deemed safe, subjects will continue to receive study medication for up to 84 days and enrollment of subjects into Dose Group 4 (0.6 mg QD) will be initiated. Following completion of the first 28 days of the treatment phase by at least 8 subjects in Dose Group 4 (0.6 mg QD), an assessment of safety and tolerability will be conducted. If Dose Group 4 is deemed acceptable, subjects will continue to receive study medication for up to 84 days.

Subjects will remain on their assigned treatment for up to 84 days. In the event a subject experiences clinically significant IP-related adverse events (AEs), a dose interruption for up to 14 days will be permitted. If a subject is unable to remain on their assigned dose, he/she will reduce their dose to the next lowest dosing regimen. Dose reductions will occur as follows:

Subjects on 0.6 mg QD will reduce their dose to 0.6 mg/0.3 mg on alternating days
Subjects on 0.6 mg/0.3 mg on alternating days will reduce their dose to 0.3 mg QD
Subjects on 0.3 mg QD will reduce their dose to 0.3 mg QOD
Subjects on 0.3 mg QOD will reduce their dose to placebo A subject will only be permitted to reduce their dose one time during the study. The decision to modify IP dosing will be based on the Investigator's clinical judgment. The sponsor should be notified of the intent to dose reduce prior to a change in dosing. Subjects who discontinue from the study prior to completing 28 days of treatment may be replaced (for up to a total of 10 subjects for Part 1) at the discretion of the sponsor.

Subjects who participate in Part 1 of the study will not be permitted to participate in Part 2 of the study.

Part 2

Part 2 is a randomized, placebo-controlled, double-blind, parallel group study to evaluate the efficacy and safety of Compound 1A in skin predominant SLE subjects. Part 2 will only be initiated once up to 8 subjects have completed 28 days of treatment in the 0.6 mg QD dose group for Part 1 and the 28 day safety assessment of the 0.6 mg QD dose group in Part 1 is completed.

Subject participation in Part 2 will consist of 3 phases:
Pre-treatment Screening Phase: up to 28 days prior to the start of the IP
Treatment Phase: Up to 84 days
Observation Phase: 84 day post-treatment Up to a total of approximately 100 subjects will be randomized into 4 dose groups of Compound 1A (0.3 mg QOD, 0.3 mg QD, 0.6 mg and 0.3 mg on alternating days and 0.6 mg QD) or matching placebo (20 subjects in each Compound 1A dosing arm and 20 subjects in the placebo arm) using an IVRS. The dose groups included in Part 2 will be dependent on results from Part 1. Any dose group which does not demonstrate adequate safety, tolerability or PD may not be used in Part 2. The treatment phase for Part 2 will be up to 84 days in duration. Subjects who discontinue IP early will enter into the observational follow-up phase for a 84 day period. In all cases of early termination from the study, subjects will be encouraged to complete an Early Termination Visit.

All subjects will be allowed to remain on stable doses of hydroxychloroquine, chloroquine, and/or quinacrine during the course of the study, provided subjects are on one of these antimalarials for ≥16 weeks prior to their baseline visit and maintain a stable dose for at least 4 weeks prior to dosing and throughout the study. No additional systemic immunosuppressives will be permitted. In addition, PRN treatment with systemic anti-pruritics and/or systemic analgesics will be permitted. However, subjects must stop using all systemic anti-pruritics 48 hours prior to all study visits and systemic analgesics 12 hours prior to all study visits. Oral NSAIDs may be used PRN, but must be stopped 12 hours prior to all study visits. Use of oral corticosteroids will be permitted only at doses of 10 mg or less per day and must be maintained at a stable dose during study participation. No IV corticosteroids will be permitted during the study. No other topical, local or systemic treatments for dermatological manifestations of SLE will be permitted.

Subjects will remain on their assigned treatment for up to 84 days. In the event a subject experiences clinically significant IP-related AEs, a dose interruption for up to 14 days will be permitted. If a subject is unable to remain on their assigned dose, he/she will reduce their dose to the next lowest dosing regimen. Dose reductions will occur as follows:

Subjects on 0.6 mg QD will reduce their dose to 0.6 mg/0.3 mg on alternating days Subjects on 0.6 mg/0.3 mg on alternating days will reduce their dose to 0.3 mg QD Subjects on 0.3 mg QD will reduce their dose to 0.3 mg QOD Subjects on 0.3 mg QOD will reduce their dose to placebo A subject will only be permitted to reduce their dose one time during the study. The decision to modify IP dosing will be based on the Investigator's clinical judgment. The sponsor should be notified of the intent to dose reduce prior a change in dosing.

Subjects who discontinue from the study prior to completing 28 days of treatment may be replaced (for up to a total of 10 subjects in Part 2) at the discretion of the sponsor.

For both Part 1 and Part 2, subjects will have regularly scheduled visits to assess IP activity and safety. Required assessments will be completed as depicted in Tables 1 and 2.

TABLE 1

Part 1

| | Pre-treatment Phase | | | | | Treatment Phase | | | Observational Follow-Up Phase | | | |
|---|---|---|---|---|---|---|---|---|---|---|---|---|
| | | | | | | Visit(s) ±1 Day - Days −28 to 29 ±2 Days - Days 43 to 169 | | | | | | |
| Day(s) | 1 Screening −28 | 2 Baseline 1 | 3 8 | 4 15 | 5 22 | 6 19 | 7-9 43, 57, 71 | 10 Final Treatment Visit/Early Termination Visit 85 | 11 Day 99 2-weeks Post-treatment | 12 Day 113 4-weeks Post-treatment | 13 Day 141 8-weeks Post-treatment | 14 Day 169 12-weeks Post-treatment |
| Study Entry | | | | | | | | | | | | |
| Informed Consent | X | — | — | — | — | — | — | — | — | — | — | — |
| Inclusion/Exclusion Criteria | X | X | — | — | — | — | — | — | — | — | — | — |
| Medical History | X | — | — | — | — | — | — | — | — | — | — | — |
| Ophthalmology Exams | X | — | — | — | — | — | — | X | — | — | — | — |
| Safety Assessments | | | | | | | | | | | | |
| Complete Physical Exam | X | — | — | — | — | — | — | X | — | X | — | X |
| Targeted Physical Exam | — | X | — | — | X | — | Day 57 | — | X | — | — | — |
| Vital Signs | X | X | X | X | — | X | X | X | X | X | X | X |
| Hepatitis B & C Screening | X | — | — | — | — | — | — | — | — | — | — | — |
| Serum Hematology, Chemistry and Urinalysis | X | X | — | X | — | X | X | X | — | X | X | X |
| IgA, IgG and IgM | — | X | — | — | — | — | Day 57 | X | — | X | — | — |
| Inflammation Panel | — | X | X | X | — | X | Day 57 | X | — | X | — | — |
| Serum β-HCG Pregnancy Test[a] | X | X | — | — | — | X | Day 57 | X | — | X | — | — |
| Urine Pregnancy Test[b] | — | X | X | X | X | X | X | — | — | — | — | — |
| Tetanus toxoid, meningococcal/, pneumococcal and influenza titer | — | X | — | — | — | — | — | X | — | — | — | — |
| Administration of tetanus toxoid, meningococcal, pneumococcal and/or influenza vaccines | — | — | X | — | — | — | — | — | — | — | — | — |
| Apolipoproteins, total cholesterol and lipid-soluble vitamins A, D, E and K | — | X | — | — | — | X | Day 57 | X | — | X | — | — |
| PT, INR and PTT | — | X | — | — | — | — | Day 43 | X | — | X | — | X |
| 12-Lead ECG | X | X | X | — | — | — | Day 43 | X | X | — | — | — |
| Adverse Events | X | X | X | X | X | X | X | X | X | X | X | X |
| Concomitant Meds and Procedures | X | X | X | X | X | X | X | X | X | X | X | X |
| Celgene Pregnancy Prevention Counseling Program (CPPCP) | X | X | — | X | — | X | X | X | X | — | — | — |

TABLE 1-continued

Part 1

|  | Pre-treatment Phase | Treatment Phase | | | | | | Observational Follow-Up Phase | | | | |
| --- | --- | --- | --- | --- | --- | --- | --- | --- | --- | --- | --- | --- |
|  |  | Visit(s) ±1 Day - Days −28 to 29 ±2 Days - Days 43 to 169 | | | | | | | | | | |
| Day(s) | 1 Screening −28 | 2 Baseline 1 | 3 8 | 4 15 | 5 22 | 6 19 | 7-9 43, 57, 71 | 10 Final Treatment Visit/Early Termination Visit 85 | 11 Day 99 2-weeks Post-treatment | 12 Day 113 4-weeks Post-treatment | 13 Day 141 8-weeks Post-treatment | 14 Day 169 12-weeks Post-treatment |
| Efficacy Assessments | | | | | | | | | | | | |
| CLASI Activity | X | X | X | X | — | X | Day 57 | X | — | X | — | — |
| CLASI Damage | — | X | — | — | — | — | Day 57 | X | — | — | — | — |
| Hybrid SELENA SLEDAI | X | X | X | X | — | X | Day 57 | X | — | X | — | — |
| Swollen and Tender Joint Count | — | X | X | X | — | X | Day 57 | X | — | X | — | — |
| PGA | — | X | X | X | — | X | Day 57 | X | — | X | — | — |
| Pericarditis/Pleuritic Pain Scale | X | X | X | X | — | X | Day 57 | X | — | X | — | — |
| HAQ-DI | — | X | X | X | — | X | Day 57 | X | — | X | — | — |
| SF-12 | — | X | — | — | — | X | Day 57 | X | — | — | X | — |
| DLQI | — | X | — | — | — | — | — | X | — | — | X | — |
| EQ-5D | — | X | — | — | — | — | — | X | — | — | — | X |
| FACIT-F | — | X | — | X | — | X | Day 57 | X | — | X | — | — |
| LupusPRO | — | X | — | — | — | — | Day 57 | X | — | X | — | — |
| PK/PD Assessments | | | | | | | | | | | | |
| Sparse PK Blood Collection | — | — | — | X | — | X | Day 57 | X | — | — | — | — |
| Intensive PK Blood Collection | — | X | — | X | — | X | Day 57 | X | — | — | — | — |
| Peripheral Blood Sample Collection for Lymphocyte Subset Analyses | — | X | — | — | — | X | Day 57 | X | — | — | — | — |
| SLE biomarker flow cytometry (aiolos and ikaros) | — | X | — | — | — | X | Day 57 | X | — | — | — | — |
| Lupus Autoantibody/Complement Panel | X | X | X | — | — | X | Day 57 | X | X | X | X | X |
| Lupus Anti-Phospholipid Profile | — | X | — | — | — | — | — | X | X | — | — | — |
| Investigational Product | | | | | | | | | | | | |
| Dispense IP | — | X | — | X | — | X | X | — | — | — | — | — |
| IP Compliance | — | — | X | X | X | X | X | X | — | — | — | — |

[a]FCBP are required to have 2 negative pregnancy tests (sensitivity of at least 25 mIU/mL) prior to starting IP. The first pregnancy test must be performed within 10 to 14 days prior to the start of IP and the second test must be performed within 24 hours of starting IP. The subject may not receive IP until the Investigator has verified that the results of these pregnancy tests are negative. FCBP with regular or no menstrual cycles must have pregnancy testing weekly for the first 4 weeks of study participation and then every 28 days while on study, at study discontinuation and at Day 28 following study discontinuation. If menstrual cycles are irregular, the pregnancy testing must occur weekly for the first 28 days and then every 14 days while on study, at study discontinuation and at Days 99 and 113 following study discontinuation.
[b]All male and FCBP subject must be counseled about pregnancy precautions and risks of fetal exposure. All subjects must also be counseled against sharing investigational product and donating blood during and within 28 days of discontinuing investigational product.

TABLE 2

Part 2

|  | Pre-treatment Phase | Treatment Phase | | | | | | Observational Follow-Up Phase | | | | |
| --- | --- | --- | --- | --- | --- | --- | --- | --- | --- | --- | --- | --- |
|  |  | Visit(s) ±1 Day - Days −28 to 29 ±2 Days - Days 43 to 169 | | | | | | | | | | |
| Day(s) | 1 Screening −28 | 2 Baseline 1 | 3 8 | 4 15 | 5 22 | 6 19 | 7-9 43, 57, 71 | 10 Final Treatment Visit/Early Termination Visit 85 | 11 Day 99 2-weeks Post-treatment | 12 Day 113 4-weeks Post-treatment | 13 Day 141 8-weeks Post-treatment | 14 Day 169 12-weeks Post-treatment |
| Study Entry | | | | | | | | | | | | |
| Informed Consent | X | — | — | — | — | — | — | — | — | — | — | — |
| Inclusion/Exclusion Criteria | X | X | — | — | — | — | — | — | — | — | — | — |
| Medical History | X | — | — | — | — | — | — | — | — | — | — | — |
| Ophthalmology Exams | X | — | — | — | — | — | — | X | — | — | — | — |

TABLE 2-continued

| | Pre-treatment Phase | Treatment Phase | | | | | | Observational Follow-Up Phase | | | |
|---|---|---|---|---|---|---|---|---|---|---|---|---|
| | | Visit(s) ±1 Day - Days −28 to 29 ±2 Days - Days 43 to 169 | | | | | | | | | | |
| Day(s) | 1 Screening −28 | 2 Baseline 1 | 3 8 | 4 15 | 5 22 | 6 19 | 7-9 43, 57, 71 | 10 Final Treatment Visit/Early Termination Visit 85 | 11 Day 99 2-weeks Post-treatment | 12 Day 113 4-weeks Post-treatment | 13 Day 141 8-weeks Post-treatment | 14 Day 169 12-weeks Post-treatment |
| Safety Assessments | | | | | | | | | | | | |
| Complete Physical Exam | X | — | — | — | — | — | — | X | — | X | — | X |
| Targeted Physical Exam | — | X | — | — | X | — | Day 57 | — | X | — | — | — |
| Vital Signs | X | X | X | X | — | X | X | X | X | X | X | X |
| Hepatitis B & C Screening | X | — | — | — | — | — | — | — | — | — | — | — |
| Serum Hematology, Chemistry and Urinalysis | X | X | — | X | — | X | X | X | — | X | X | X |
| IgA, IgG and IgM | — | X | — | — | — | — | Day 57 | X | — | X | — | — |
| Inflammation Panel | — | X | X | X | — | X | Day 57 | X | — | X | — | — |
| Serum β-HCG Pregnancy Test[a] | X | X | — | — | — | X | Day 57 | X | — | X | — | — |
| Urine Pregnancy Test[b] | — | X | X | X | X | X | X | — | — | — | — | — |
| Tetanus Toxoid, meningococcal, pneumococcal and influenza titer | — | X | — | — | — | — | — | X | — | — | — | — |
| Administration of tetanus toxoid, meningococcal/pneumococcal and/or influenza vaccines | — | — | X | — | — | — | — | — | — | — | — | — |
| Apolipoproteins, total cholesterol and lipid-soluble vitamins A, D, E and K | — | X | — | — | — | X | Day 57 | X | — | X | — | — |
| PT, INR and PTT | — | X | — | — | — | — | Day 43 | X | — | X | — | X |
| 12-Lead ECG | X | X | X | — | — | — | Day 43 | X | X | — | — | — |
| Adverse Events | X | X | X | X | X | X | X | X | X | X | X | X |
| Concomitant Meds and Procedures | X | X | X | X | X | X | X | X | X | X | X | X |
| Celgene Pregnancy Prevention Counseling Program (CPPCP) | X | X | — | X | — | X | X | X | X | — | — | — |
| Efficacy Assessments | | | | | | | | | | | | |
| CLASI Activity | X | X | X | X | — | X | Day 57 | X | — | X | — | — |
| CLASI Damage | — | X | — | — | — | — | Day 57 | X | — | — | — | — |
| Hybrid SELENA SLEDAI | X | X | X | X | — | X | Day 57 | X | — | X | — | — |
| PGA | — | X | X | X | — | X | Day 57 | X | — | X | — | — |
| Swollen and Tender Joint Count | — | X | X | X | — | X | Day 57 | X | — | X | — | — |
| Pericarditis/Pleuritic Pain Scale | X | X | X | X | — | X | Day 57 | X | — | X | — | — |
| HAQ-DI | — | X | X | X | — | X | Day 57 | X | — | X | — | — |
| SF-12 | — | X | — | — | — | X | Day 57 | X | — | — | X | — |
| DLQI | — | X | — | — | — | — | — | X | — | — | X | — |
| EQ-5D | — | X | — | — | — | — | — | X | — | — | — | X |
| FACIT-F | — | X | — | X | — | X | Day 57 | X | — | X | — | — |
| LupusPRO | — | X | — | — | — | — | Day 57 | X | — | X | — | — |
| PK/PD Assessments | | | | | | | | | | | | |
| Sparse PK Blood Collection | — | — | — | X | — | X | Day 57 | X | — | — | — | — |
| Intensive PK Blood Collection | — | X | — | X | — | X | — | — | — | — | — | — |
| Peripheral Blood Sample Collection for Lymphocyte Subset Analyses | — | X | — | — | — | X | Day 57 | X | — | — | — | — |
| SLE biomarker flow cytometry (aiolos and ikaros) | — | X | — | — | — | — | — | — | — | — | — | — |
| Lupus Autoantibody/Complement Panel | X | X | X | — | — | X | Day 57 | X | X | X | X | X |
| Lupus Anti-Phospholipid Profile | — | X | — | — | — | — | — | X | X | — | — | — |
| Pharmacogenetic Blood Collection | — | X | — | — | — | — | — | — | — | — | — | — |
| Dispense IP | — | X | — | X | — | X | X | — | — | — | — | — |
| IP Compliance | — | — | X | X | X | X | X | X | — | — | — | — |

[a]FCBP are required to have 2 negative pregnancy tests (sensitivity of at least 25 mIU/mL) prior to starting IP. The first pregnancy test must be performed within 10 to 14 days prior to the start of IP and the second test must be performed within 24 hours of starting IP. The subject may not receive IP until the Investigator has verified that the results of these pregnancy tests are negative. FCBP with regular or no menstrual cycles must have pregnancy testing weekly for the first 4 weeks of study participation and then every 28 days while on study, at study discontinuation and at Day 28 following study discontinuation. If menstrual cycles are irregular, the pregnancy testing must occur weekly for the first 28 days and then every 14 days while on study, at study discontinuation and at Days 99 and 113 following study discontinuation.
[b]All male and FCBP subject must be counseled about pregnancy precautions and risks of fetal exposure. All subjects must also be counseled against sharing investigational product and donating blood during and within 28 days of discontinuing investigational product.

Upon completion of, or discontinuation from the Treatment Phase for Part 1 or Part 2, all subjects (including premature discontinuations) will be followed bi-weekly for the first 28 days and then monthly for the remaining 56 days in a 28 day Observational Follow-up Phase. This study will be conducted in compliance with the protocol, good clinical practice (GCP) and applicable regulatory requirements.

6.2.2. Study Population

The study population consists of male and female subjects 18 years of age and older at the time of signing the ICD for both Part 1 and Part 2.

Subjects in Part 1 are required to have an established diagnosis of SLE as defined by the 1997 Update of the 1982 American College of Rheumatology (ACR) Revised Criteria for Classification of SLE at Screening.

Subjects in Part 2 are required to have:
An established diagnosis of SLE as defined by the 1997 Update of the 1982 ACR Revised Criteria for Classification of SLE at Screening
A clinical diagnosis of SLE with dermatologic manifestations of lupus disease for at least 16 weeks prior to screening, and consistent findings on skin biopsy based on Gilliam classification
Active skin lesions of sufficient severity, based on the Cutaneous Lupus Area and Severity Index (CLASI) (CLASI Activity Score ≥10) at Baseline
Active SLE arthritis defined as at least 3 tender joints at Baseline
Positive antibodies associated with SLE, which must include one of the following:
Anti-nuclear Antibodies (ANA) defined as a titer of 1:160 or greater via Immunoflourescence Assay (IFA) within the Screening period
Positive ds-DNA antibodies defined as ≥30 IU within the Screening period
Anti-nuclear antibodies (SS-A [Ro], SS-B(La), Smith or RNP) within the Screening period 6.2.3 Length of Study The length of study participation for each subject is 196 days (Up to a 28 day Screening Phase, 84 day Treatment Phase and a 84 day Observational Follow-Up Phase) for both Part 1and Part 2 participants.

The End of Trial is defined as either the date of the last visit of the last subject to complete the study, or the date of receipt of the last data point from the last subject that is required for primary, secondary and/or exploratory analyses, as pre-specified in the protocol and/or the Statistical Analysis Plan, whichever is the later date.

6.2.4. Study Treatment

Compound 1A will be provided as 0.3 mg capsules. Standard matching placebo capsules will also be provided. Capsules will be taken by mouth (PO) with or without food.

Subjects will be randomized to one of the 4 following dose groups for Part 1. If all four dose groups demonstrate sufficient safety, tolerability and/or efficacy during Part 1, the same four dose groups will be used for Part 2. Investigational product will be administered PO as described below:
Compound 1A
0.3 mgQOD
Subjects will receive 0.3 mg once every other day
0.3 mgQD
Subjects will receive 0.3 mg every day
0.6 mg and 0.3 mg on alternating days
Subjects will receive 0.6 mg and 0.3 mg on alternating days.
0.6 mgQD
Subjects will receive 0.6 mg every day
Placebo
Subjects assigned to the placebo group will receive matching placebo capsule(s) daily. In the event a subject on placebo experiences clinically significant IP-related AEs, a dose interruption for up to 14 days will be permitted. If a subject is unable to remain on their placebo, the subject may discontinue IP early and enter into either an 84 day observational follow-up phase for Part 1 or a 28 day follow-up phase for Part 2. In all cases of early termination from the study, subjects will be encouraged to complete an Early Termination Visit. The decision to modify IP dosing will be based on the Investigator's clinical judgment. The sponsor should be notified of the intent to dose reduce prior a change in dosing. In the event that a subject experiences a flare during the observational follow-up period, the PI may treat the subject with the standard of care in order to allow the subject to remain in the study and continue with the scheduled visits and assessments indicated by the schedule of assessments.

6.2.5 Overview of Safety Assessments

Safety is assessed based on the following criteria:
Adverse events
Vital signs, including height, weight, pulse, temperature and blood pressure
Hematology, serum chemistry, urinalysis
Inflammation panel
Serum beta-human chorionic gonadotropin (HCG) and urine pregnancy tests (for females of childbearing potential [FCBP])
Tetanus toxoid, meningococcal, pneumococcal and influenza vaccine titers
Centralized 12-lead electrocardiograms (ECGs)
Physical examinations, including height and weight
Concomitant medications and procedures
Ophthalmological exams
Hepatitis screening 6.2.6 Overview of Pharmacokinetic Assessments Blood samples for quantification of Compound 1A in plasma will be taken at specified time points (Tables 1 and 2) during the course of the study. A minimum of 4 subjects in each of the 4 treatment groups in Part 1 and Part 2 (minimum total of 32 subjects) will be targeted for participation in the intensive PK portion of the study. The IVRS will be used to ensure inclusion of a minimum of 4 intensive PK participants per dose group. Noncompartmental PK parameters of Compound 1A will be estimated from these subjects. All other subjects who do not participate in the intensive PK portion of the study will have sparse PK samples collected.

6.2.7 Overview of Pharmacodynamic Assessments

Pharmacodynamic profile is assessed based on the following:
The PD markers aiolos and ikaros will be measured in peripheral white blood cells in Part 1 and Part 2
Peripheral blood lymphocyte subsets will be measured will be measured in Part 1 and Part 2
Lupus Autoantibody/Complement Panel (anti-Ro, anti-La anti-dsDNA, anti-smith, rheumatoid factor, anti-RNP, C3, C4, cell-bound complement activated products (CB-CAPs), CH50, ANA, ANCA, anti-thyroid antibodies) in Part 1 and Part 2

6.2.8 Overview of Efficacy Assessments

Efficacy is assessed based on the following:
Cutaneous Lupus Area and Severity Index (CLASI)

Hybrid SELENA Systemic Lupus Erythematosus Disease Activity Index (SLEDAI)

Physician's Global Assessment (PGA)

Swollen and Tender Joint Counts

Pericardial/Pleuritic Pain Numerical Rating Scale 6.2.9 Overview of Quality-of-Life Assessments Overall quality of life is assessed based on the following:

Functional Assessment of Chronic Illness Therapy-Fatigue (FACIT-F)

Short form-12 (SF-12)

EQ-5D

Dermatology Life Quality Index (DLQI)

Disability Index of the Health Assessment Questionnaire (HAQ-DI)

Lupus Patient Reported Outcome Tool (LupusPRO)

6.2.10 Overview of Pharmacogenetic Assessments

Pharmacogenetic profile can be assessed using Single Nucleotide Polymorphisms in genes associated with SLE, such as, but not limited to IKZF1 and IKZF3.

6.2.11 Procedures

A. Study Entry

Required assessments will be completed as depicted in Tables 1 and 2.

Informed consent must be obtained by the principal investigator or designee for all subjects prior to the initiation of any study procedures. All subjects must review the sub-study portion of the ICD (intensive PK, immunization and PG) prior to the initiation of any study procedures and indicate whether or not they consent to participate in this portion of the study.

Relevant medical history (including relevant GI symptoms, neurological symptoms, alcohol and tobacco use, etc.) information will be collected for each subject.

Information regarding prior/concomitant medication usage will be collected for each subject. At the screening and baseline visits, concomitant medications should be checked against the list of prohibited medications to ensure required washout times have been met. If a subject does not meet the medication washout requirements, the study visit must be rescheduled.

B. Safety Assessment

On the days of study visits, subjects will take their IP dose at the site.

Required assessments will be completed as depicted Tables 1 and 2. Assessments may be conducted at other times during the study if felt to be clinically warranted by the Investigator.

Information regarding all AEs regardless of causal relationship to IP (Compound 1A or placebo), occurring at any time for the duration of the study, from the time of signing the ICD up to and including the Observation Phase, will be collected.

Vital signs include temperature, pulse, and seated blood pressure. Blood pressure will be measured after the subject has been seated and resting quietly for 5 minutes.

On study visits where ECGs and PK evaluations are performed, blood pressure measurements should be completed first. Pre-dose ECGs should then be performed, followed by pre-dose PK blood draws and IP dosing.

Complete physical examinations will include height (Screening visit) and weight (Screening and the Final Treatment Visit—to be done in street clothes, no shoes), skin, nasal cavities, eyes, ears, respiratory, cardiovascular, gastrointestinal, neurological, lymphatic, and musculoskeletal system evaluations. Results of the physical examinations will be recorded only in the source documents. Clinically significant abnormal findings identified during the Screening physical examination will be recorded on the e-CRF as medical history; clinically significant findings identified during the final treatment visit physical examination will be recorded as adverse events. Gynecological and urogential examinations will not be done unless for cause.

Targeted physical examinations will include evaluation of the skin, respiratory, cardiovascular, lymphatic, and musculoskeletal systems. Results of the physical examinations will be recorded only in the source documents. Clinically significant abnormal findings identified during the targeted physical examinations will be recorded on the eCRF as adverse events. Gynecological and urogenital examinations will not be done unless for cause.

Standard 12-lead ECGs will be obtained at most study visits. In cases where ECG and PK timepoints coincide, a ±15 minute window will be allowed for assessment completion (ECG should always be assessed first). All ECGs from Visit 2 onward should be performed 5 minutes apart after the subject has been in the supine position for 3 minutes.

At Screening: one ECG will be performed

At required treatment visits: 3 ECGs will be done pre-dose

In the Observational Follow-Up Phase: one ECG will be performed Stimulatory agents and/or medications, e.g., caffeine, energy drinks, licorice, theophylline, etc, should be avoided prior to ECG administration. The same ECG equipment will be used throughout the study. All ECG recordings will be manually over-read on an ongoing basis by a cardiologist at the core ECG laboratory for QT measurement and QTc calculation using Bazett's and Fridericia's formula.

Laboratory Assessments

Pregnancy testing (urine and/or serum) for all FCBP

Serum chemistry (including total protein, albumin, calcium, phosphorus, glucose, uric acid, total bilirubin, alkaline phosphatase, AST [SGOT], ALT [SGPT], lipase, sodium, potassium, chloride, bicarbonate, blood urea nitrogen, creatinine, lactate dehydrogenase, [LDH], magnesium)

Hematology (complete blood count with differential and platelets, absolute white blood cell counts, apolipoproteins, total cholesterol)

Lipid-soluble vitamins (A, D, E, K)

PT, INR and PTT

Urinalysis (microscopic and quantitative protein)

Tetanus toxoid, meningococcal, pneumococcal and influenza titers

Inflammation panel (including erythrocyte sedimentation rate [ESR], fibrinogen, high sensitivity C-reactive protein [hs-CRP], serum amyloid A)

Hepatitis screen (includes testing for Hepatitis B surface antigen and antibody, Hepatitis B core antibodies (IgG/IgM) and antibodies to Hepatitis C)

Quantitative assessment of immunoglobulins [immunoglobulin A (IgA), immunoglobulin M (IgM), and immunoglobulin G (IgG)]

Lupus Anti-Phospholipid Profile (lupus anticoagulant, anti-cardiolipin antibodies, antibodies to beta-2-glycoprotein I and phosphatidylserine)

Detailed instructions for sample collection, processing, storage, shipping and handling will be provided to the sites in a separate manual.

Ophthalmological examinations will be conducted by a qualified ophthalmologist. Testing will include visual acuity and slit lamp exams with fluorescein staining following pupillary dilation, focusing on the anterior chamber, iris and anterior vitreous (unless use of fluorescein is contraindicated, e.g. due to hypersensitivity).

Celgene Pregnancy Prevention Counseling Program (CP-PCP).

C. Efficacy Assessments

In the event that a subject has taken systemic analgesics within 12 hours of a study visit and/or systemic anti-pruritics within 48 hours of a visit, their visit should be rescheduled. Health assessment questionnaires must be completed prior to any other study activities so that responses most accurately reflect subjects' experiences before the study visit. If the subject needs help in completing the questionnaires, assistance should only be provided by study staff and not by family members. CLASI, DAS28, Hybrid SELENA SLEDAI and PGA assessments should be conducted by the same trained Investigator or sub-investigator throughout the study.

CLASI Activity Score Assessment

The CLASI Activity Score ranges from 0 to 70. To generate the activity score erythema is scored on a scale of 0 (absent) to 3 (dark red; purple/violaceous/crusted/hemorrhagic) and scale/hypertrophy are scored on a scale of 0 (absent) to 2 (verrucous/hypertrophic). Both the erythema and scale/hypertrophy scores are assessed in 13 different anatomical locations. In addition, the presence of mucous membrane lesions is scored on a scale of 0 (absent) to 1 (lesion or ulceration), the occurrence of recent hair loss is captured (1=yes; 0=no) and non-scarring alopecia is scored on a scale of 0 (absent) to 3 (focal or patchy in more than one quadrant). To calculate the activity score, all scores for erythema, scale/hypertrophy, mucous membrane lesions and alopecia are added together.

CLASI Damage Score Assessment

The CLASI Damage Score ranges from 0 to 56. To generate the damage score, dyspigmentation is scored on a scale of 0 (absent) to 1 (dyspigmentation) and scarring/atrophy/panniculitis are scored on a scale of 0 (absent) to 2 (severely atrophic scarring or panniculitis). Both the dyspigmentation and scarring/atrophy/panniculitis scores are assessed as usually lasting greater than or less than 12 months for the subject. If the dyspigmentation usually lasts greater than 12 months, the dyspigmentation scoring conducted for the 13 anatomical areas is doubled. In addition, scarring of the scalp (judged clinically), is scored on a scale of 0 (absent) to 6 (affects the whole skull). To calculate the damage score, all scores for dyspigmentation, scarring/atrophy/panniculitis, and scarring of the scalp are added together.

Physician Global Assessment (PGA)

The PGA uses a visual analog scale with scores between 0 and 3 to indicate worsening of disease. The scoring is as follows:

0=none
1=mild disease
2=moderate disease
3=severe disease

This is a physician administered instrument used to gauge a subject's overall state of health. A 10% increase (0.3 points) is considered a clinically relevant worsening of disease.

Swollen and Tender Joint Count

Using this tool, joint tenderness and swelling will be noted as "present" or "absent," with no quantitation of severity. In order to maintain consistency throughout the study, the same evaluator should perform the joint assessments for a given subject at a study site at each study visit.

Hybrid SELENA SLEDAI

The hybrid SELENA SLEDAI measures disease activity through assessment of 24 lupus manifestations using a weighted score of 1 to 8 points. A decrease of 4 or greater points in the Hybrid SELENA SLEDAI is considered clinically meaningful. A manifestation is recorded if it is present over the previous 10 days regardless of severity or whether it has improved or worsened. What differentiates the hybrid SELENA SELEDAI from the SELENA SLEDAI is the definition of proteinuria. The Hybrid SELENA SLEDAI defines proteinuria as >0.5 gm/24 hours—'new onset or recent increase of more than 0.5 gm/24 hours' has been removed from the definition.

Pericarditis/Pleuritic Numerical Pain Scale

Each scale is scored using numerical values of 1 through 10—1 representing 'no pain' and 10 representing 'worst possible pain'. Both pain scales will be self-administered by the subject and gauge the severity of their SLE pain related to pericardial and pleuritic discomfort. Any indication from subjects or study assessments, aside from pain, which indicate clinically significant pericardial or pleuritic manifestations of SLE must be thoroughly investigated. If clinically significant SLE related complications are found, the subject should be discontinued from the study into the Observational Follow-Up Period and treated appropriately.

D. QoL Assessments

Required assessments will be completed as depicted in Tables 1 and 2.

SF-12

The SF-12 is a self-administered instrument consisting of 8 multi item scales that assess 8 health domains: 1) limitations in physical activities because of health problems; 2) limitations in social activities because of physical or emotional problems; 3) limitations in usual role activities because of physical health problems; 4) bodily pain; 5) general mental health (psychological distress and well-being); 6) limitations in usual role activities because of emotional problems; 7) vitality (energy and fatigue); and 8) general health perceptions. The concepts measured by the SF-12 are not specific to any age, disease, or treatment group, allowing comparison of relative burden of different diseases and the relative benefit of different treatments.

FACIT-F

The FACIT-Fatigue scale is a 13-item self-administered questionnaire that assesses both the physical and functional consequences of fatigue. Each question is answered on a 5-point scale, where 0 means "not at all," and 4 means "very much." Higher scores denote higher levels of fatigue. It is expected that the FACIT-Fatigue score will decrease as improvements are made in subjects' SLE.

EQ-5D

The EQ-5D measures the subject's general health state as a vertical VAS and 6 quality of life domains as multiple choice questions: mobility, self-care, main activity (work, study, housework), family/leisure activities, pain/discomfort, and anxiety/depression, the combination of which generates 216 possible health states.

DLQI

DLQI will be assessed by the subject upon arrival at the site before any other procedures or assessments are performed. The DLQI was developed as a simple, compact, and practical questionnaire for use in a dermatology clinical setting to assess limitations related to the impact of skin disease. The instrument contains ten items dealing with the subject's skin. With the exception of Item Number 7, the subject responds on a four-point scale, ranging from "Very Much" to "Not at All." Item Number 7 is a multi-part item, the first part of which ascertains whether the subject's skin prevented them from working or studying (Yes or No), and if "No," then the subject is asked how much of a problem the skin has been at work or study over the past week, with response alternatives being "A lot," "A little," or "Not at all." The DLQI Total score has a possible range of 0 to 30, with 30 corresponding to the worst quality of life, and 0 corresponding to the best score. The developers suggest that the DLQI can be grouped into six subscales: symptoms and feelings; daily activities; leisure; work/school; personal relationships; and treatment. Scores for four of the subscales (symptoms and feelings, daily activities, leisure, and personal relationships) range from 0 to 6; scores for two of the subscales (work/school and treatment) range from 0 to 3. Higher scores correspond to poorer quality of life.

LupusPRO

The LupusPRO is a disease targeted patient reported outcome tool for patients with SLE. It was developed from ethnically diverse US patients with SLE. It has been validated for use in the US. It has 43 items of which 30 items are for health related quality of life (Jolly, 2007; Jolly, 2008; Cervera, 2010).

Disability Index of the Health Assessment Questionnaire (HAQ-DI)

The HAQ-DI is a 20-question, self-administered instrument that measures the subject's functional ability on a 4-level difficulty scale (0 to 3, with 0 representing normal or no difficulty; and 3 representing an inability to perform). Eight categories of functioning are included: dressing, rising, eating, walking, hygiene, reach, grip, and usual activities (Bruce et al., *J. Rheumatol.*, 2003, 30:167-78). This scale is sensitive to change and is a good predictor of future disability (Aletaha et al., *Rheum. Dis. Clin. North Am.*, 2006, 32:9-44).

E. Other Assessments—Pharmacokinetics

All subjects will participate in sparse PK as a participant in the main study. Completion of intensive pharmacokinetics requires the subject to have consented using the sub-study informed consent form. Both intensive and sparse PK samples will be collected to evaluate Compound 1A PK. Intensive PK samples may also be measured for the R-enantiomer. Dosing and sample collection information including Compound 1A dose level, dosing date, dosing time (24 hour clock), and actual PK blood sampling time (24 hour clock) should be accurately documented on the appropriate eCRF pages.

Spare PK Sampling

All other subjects who do not participate in the intensive PK portion of the study will have sparse PK samples collected. Pharmacokinetic blood samples (approximately 12 mL total) will be collected in subjects (unless the site does not have PK capabilities) who do not participate in intensive PK sampling at the following time points: Days 15, 29, 57 and 85: one pre-dose sample per visit.

Intensive PK Sampling

Participation in the intensive PK assessment will be an optional sub-study for which a separate consent will be signed at screening. Frequent collection of PK blood samples (approximately 57 mL total) will be performed in a minimum of 4 subjects per treatment group (a total of 32 subjects at the minimum) at the following time points:

Visit 2 (Baseline—Day 1): predose (Time=0), 1, 2, 3, 4, between 6 and 8 hours and 24 hours (±5 hours) after administration of IP.

Visit 4 (Day 15): one predose sample per visit

Visit 6 (Day 29): predose (Time=0), 1, 2, 3, 4, between 6 and 8 hours and 24 hours (±5 hours) after administration of IP.

Visits 8 and 10 (Days 57 and 85): one predose sample per visit

The IVRS will be used to ensure inclusion of a minimum of 4 intensive PK participants per dose group. Pharmacokinetic samples should be collected within the following collection windows:

−30 to −5 minutes for the pre-dose sample

±10 minutes for the samples collected at timepoints of 1-4 hours

±20 minutes for the samples collected at the timepoint of between 6 and 8 hours

±5 hours for the sample collected at the timepoint of 24 hours (this sample must be collected prior to the second dose)

At each time point, approximately 3 mL blood will be collected. The concentration of Compound 1A in plasma will be determined.

On all PK visits, subjects must bring their IP to the study center and IP must be administered to subjects at the study center after the collection of the predose PK blood sample. Subjects will be asked to report the date and time of their last IP dose (prior to the current study visit day) to the study staff during their visit at the study center. The IP dosing time on the day of the PK sample collection should also be documented by the study staff.

In cases where ECG and PK time points coincide, a ±15 minute window will be allowed for completion of PK (the ECG should always be assessed first).

F. Other Assessments—Pharmacodynamics

Peripheral Blood Biomarkers

PD blood biomarker measurements will be collected as follows:

Drug Target Engagement: Peripheral blood aiolos and ikaros by flow cytometry at Day 1, Day29, Day57 and Day85 in Part 1 and Day 1 in Part2

Immune System: Peripheral blood B cells, T cells, CD3+, CD4+, CD8+, CD16+/56, CD 19+ lymphocyte subsets, and dendritic cells (DC) by flow cytometry at Day 1, Day 29, Day 57 and Day 85

Disease Markers: Lupus Autoantibody/Complement Panel (anti-Ro, anti-La anti-dsDNA, anti-smith, rheumatoid factor, anti-RNP, C3, C4, CB-CAPs, CH50, ANA, ANCA, anti-thyroid antibodies) at Day 1, 8, 29 57 and Day 85 (or Early Termination), and Days 113, 141 (Part 1 only) and 169 (Part 1 only) of the Observational Follow-up Phase G. Other Assessments—Pharmacogenics Participation in the PG assessment will be an optional sub-study for which a separate consent will be signed at screening. The attempt is to obtain as many subjects as reasonable. A single blood sample will be obtained at baseline for the genetic analysis to assess genetic markers associated with Compound 1A efficacy or safety. Pharmacogenetic testing will be conducted using DNA isolated from blood drawn at baseline. DNA will be examined for the presence of polymorphisms in or near the genes associated with SLE (including but not limited to the following genes: IKZF1 (gene encoding Ikaros), IKZF3 (gene encoding Aiolos), PRDM1 (gene encoding BLIMP-1), HLA-DRB1, BLK, BANK1, TNFAIP3, STAT4, IRF5, TNFSF4, TRIM27, OR2H2, MICB, CREBL1, HSD17B, JAZF1, ATG5, PTTG1, PXK, ITGAM, ETS1, LRRC18-WDFY4, RASGRP3, SLC15A4, TNIP1, IRF8, IL10, NCF2, IFIH1, TYK2, and the Compound 1A target-related genes CRBN (gene encoding cereblon) and CUL4A.

H. Other Assessments—Immunization

Participation in the Immunization sub-study will be optional for which a separate consent will be signed at screening. The effect of Compound 1A on immunizations in SLE subjects will be monitored by measuring tetanus toxoid, meningococcal and pneumococcal titers during the study. Subjects who qualify (based upon their medical history) will have the opportunity to participate in an immunization sub-study where they will receive tetanus toxoid and meningococcal or pneumococcal immunizations at the start of the treatment period.

Subjects who agree participate in the immunization sub-study must qualify for each vaccination type according to the following set of criteria:

Tetanus Toxoid
  Receipt of vaccine was less than 5 years prior to baseline
  It is safe to provide to the subject per the investigator's judgment Meningococcal/pneumococcal
  The subject can receive only the pneumococcal or the meningococcal vaccine—not both. If the subject has not received either vaccine within 5 years prior to the Baseline Visit, only the pneumococcal vaccine should be given. Subjects will only be eligible for the meningococcal vaccine if they have received the pneumococcal vaccine within 5 years of the Baseline Visit and they have not received the meningococcal vaccine within 5 years of the Baseline Visit. If the subject has also received the meningococcal vaccine within 5 years of the Baseline Visit they will not be eligible to receive either vaccine.
  It is safe to provide to the subject per the investigator's judgment

6.3 Example 3: Overexpression of CRBN, IKZF1 and IKZF3 MRNA in SLE PBMC

Viably frozen PBMCs from healthy volunteers (N=10) or SLE patients (N=11) were obtained from Conversant Bio (Huntsville, Ala.). Cells were quickly thawed in 37° C., washed in PBS, pelleted with centrifugation, and immediately lysed in RLT buffer. Total RNA was purified with RNeasy mini spin-column kits (Catalog #74104) using QIAcube™ system (Qiagen, Valencia, Calif.). Purified RNA was reverse transcribed into cDNA using a reverse-transcriptase kit (Applied Biosystems). Real-time quantitative RT-PCR was performed using Taqman® PCR probes specific for CRBN (A), IKZF1 (B), and IKZF3 (C) in ViiA7 real time polymerase chain reaction (RT-PCR) system (Applied Biosystems) in duplicates. The quantity of product was normalized to glyceraldehyde-3-phosphate dehydrogenase as the endogenous housekeeping gene. Fold increase of gene expression was calculated using comparative Ct method ($2^{-\Delta\Delta Ct}$). P values were generated using an unpaired t test.

Figure 2A:
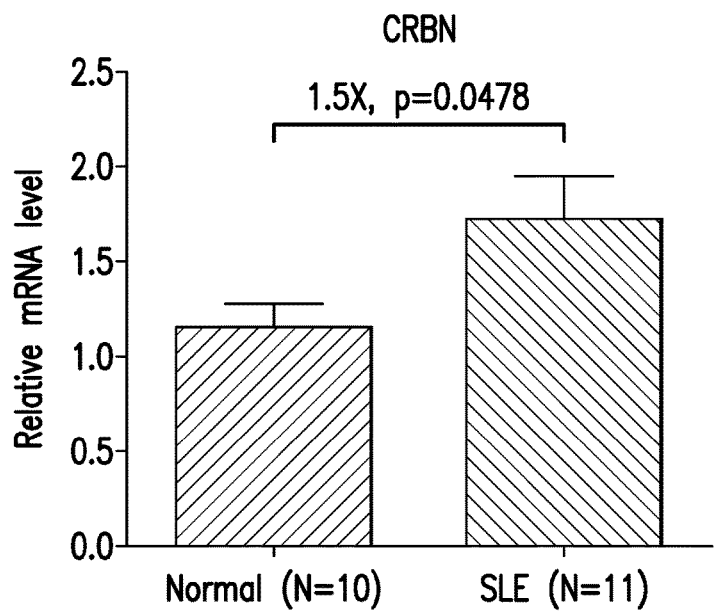
Figure 2B:
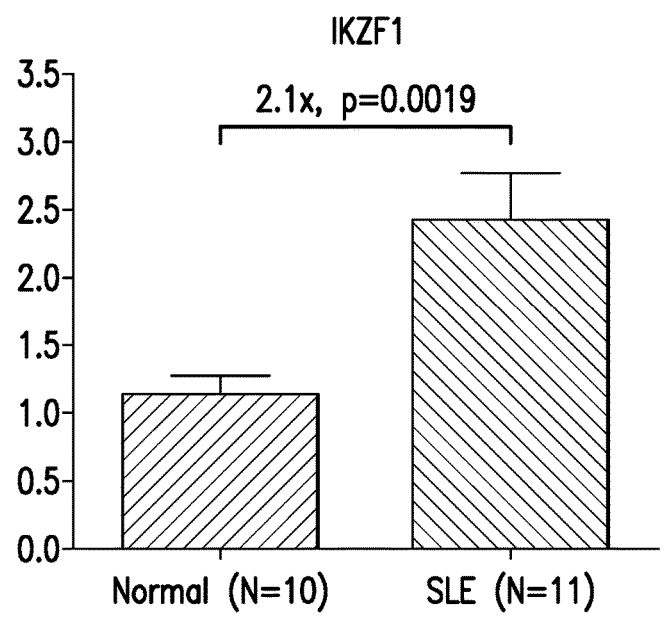
Figure 2C:
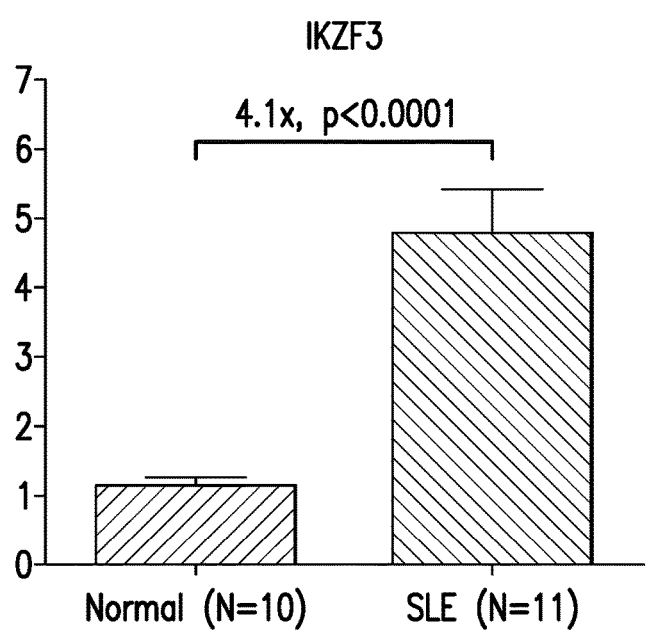

Expression of Genes encoding Cereblon (CRBN), Ikaros (IKZF1), and Aiolos (IKZF3) in peripheral blood mononuclear cells from SLE patients compared to normal controls is depicted in FIG. 2A, FIG. 2B, and FIG. 2C, respectively. The results demonstrate overexpression of CRBN, IKZF1 and IKZF3 mRNA in SLE PBMC. Compared to normal PBMC (N=10), SLE PBMC (N=11) expressed significantly higher levels of cereblon (CRBN), Ikaros (IKZF1), and Aiolos (IKZF3).

6.4 Example 4: Effects of Compound 1a on Aiolos and Ikaros Protein Levels

Human heparinized whole blood from normal healthy volunteers (Bioreclamation, Westbury, N.Y.) was treated with 0.1% DMSO and Compound 1A (1, 10, 100 nM) for 18 hrs at 37° C., 5% $CO_2$. After 18 hrs, the blood was lysed and fixed with 1× Lyse/Fix Buffer (BD Biosciences) for 10 minutes at 37° C. Washed cells with cold PBS and cells were first multicolor stained with mouse anti-human CD3-PE mAb, mouse anti-human CD19-APC mAb and mouse anti-human-CD14-PerCP mAb (all from BD Biosciences) to identify CD3+ T cells, CD19+ B cells and CD14+ monocytes, respectively. The cells were then permeabilized by adding BD Perm/Wash Buffer I. Blocked non-specific binding by added FcR Blocking Reagent (Miltenyi Biotech) for 10 minutes prior to staining for intracellular Aiolos or Ikaros content. The cells were then stained with rabbit anti-human Aiolos polyclonal Ab (Santa Cruz, 1:200 dilution in Perm/Wash Buffer) or anti-human Ikaros polyclonal Ab (Santa Cruz, 1:50 dilution in Perm/Wash Buffer), followed by a goat-anti-rabbit mAb-AF488 Ab (Invitrogen, at 1:400 dilution in Perm/Wash Buffer) to test the intracellular Aiolos or Ikaros levels. Normal rabbit IgG (R&D Systems) was also used as isotype control. Aiolos and Ikaros protein levels in B cells, T cells, monocytes and granulocytes were analyzed by FACSCanto with FACSDiva 6 (BD Biosciences) based on the gating of CD3+cells, CD19+ cells, CD14+ cells and granulocytes (FSC/SSC). Data analysis was performed using Flowjo (Tree Star) software.

Figure 3A:
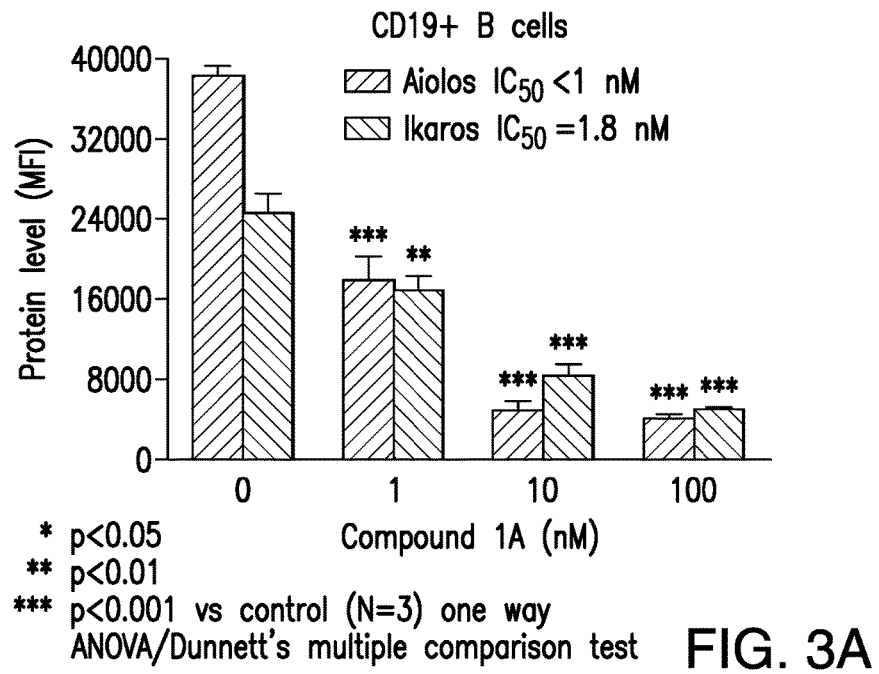
Figure 3B:
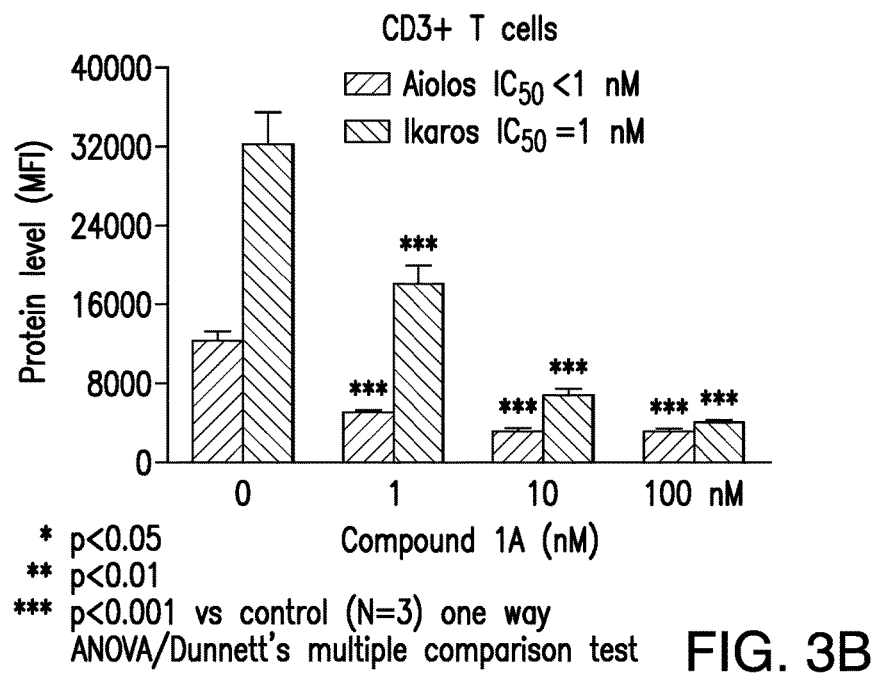
Figure 3C:
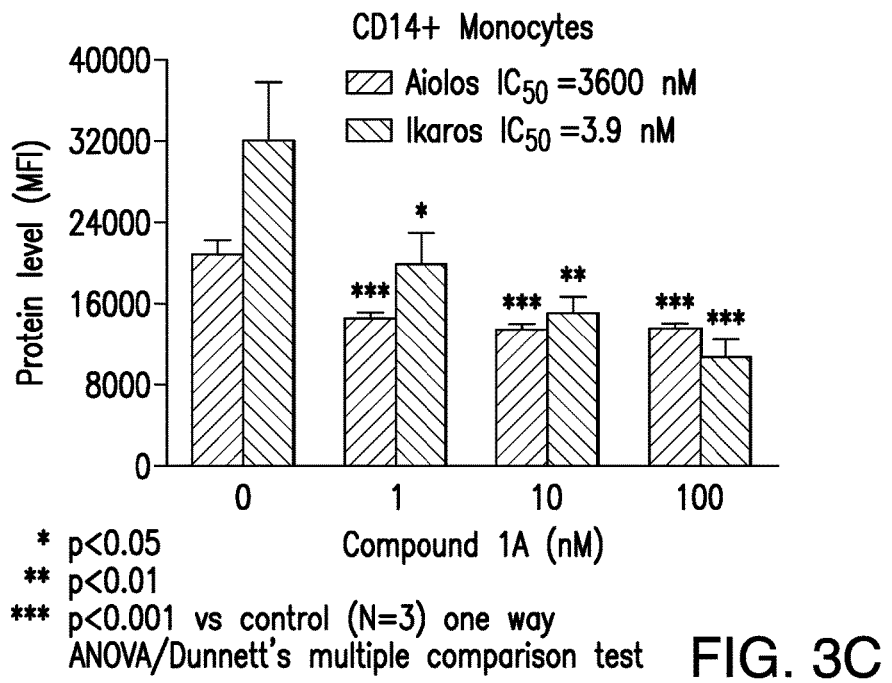
Figure 3D:
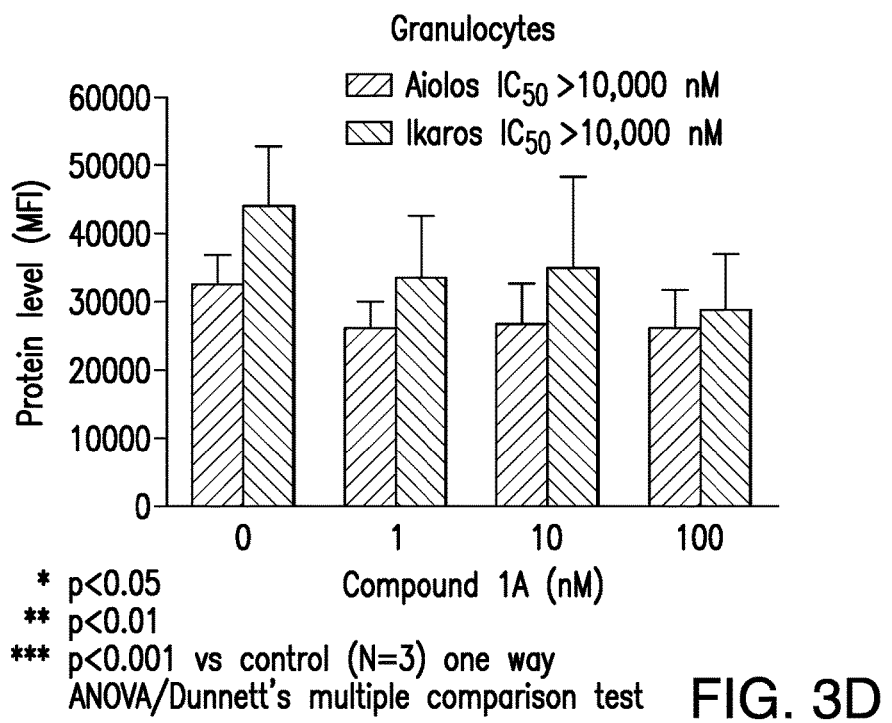

The results demonstrate that Compound 1A reduced Aiolos and Ikaros protein levels in whole blood leukocyte subsets including CD19+ B cells (FIG. 3A), CD3+ T cells (FIG. 3B), CD14+ monocytes (FIG. 3C), and granulocytes (FIG. 3D).

PBMCs were purified from human buffy coats using Ficoll-Paque method. CD19+ B cells were isolated from PBMC by following EasySep Human B cell enrichment cocktail protocol (StemCell Technologies Catalog #19054). Fresh B cell cocktail was prepared by adding 50 μg/mL of human transferrin to B cell medium (Iscove's medium with 10% PFBS, 1% P/S, and 5 μg/mL human insulin). The required volume of medium needed for the experiment was filtered through a 0.22 micron filter. B cell differentiation cocktail (final concentration): recombinant human Interleukin (IL)-2 (20 U/mL), IL-10 (50 ng/mL), IL-15 (10 ng/mL), CD40 Ligand/TNFSF5/histidine-tagged (50 ng/mL), poly-Histidine mouse IgG1 antibody (5 μg/mL), and ODN 2006-Human TLR9 ligand (10 μg/mL). CD19+ cells were pre-treated with Compound 1A or a Syk inhibitor or 0.1% DMSO for 1 hr, then incubated with B-cell differentiation medium for indicated times.

Following incubation, cells were collected, pelleted with centrifugation, and immediately lysed in 0.1 mL lysis buffer containing 10 mM Tris-HCl pH 8.0, 10 mM EDTA, 150 mM NaCl, 1% NP-40, 0.5% SDS, 1 mM DTT, 1 mM Na3VO4, plus Complete™ protease inhibitor cocktail (Roche Applied Science, Indianapolis, Ind.), then processed with a QIAshredder™ (Qiagen) for 1 minute and frozen on dry ice. Samples were diluted with 6×SDS sample buffer and then boiled for 5 minutes. Approximately 15 μL of this mixture was loaded per lane on a Criterion Precast 10% Tris-HCl gel (Bio-Rad Laboratories, Hercules, Calif.), electrophoresed, and transferred to nitrocellulose membranes (Bio-Rad). The membranes were blocked for 1 hour at room temperature using blocking buffer (LI-COR Biosciences, Lincoln, Nebr.), then incubated overnight at 4° C. with antibodies against either Aiolos, Ikaros, or β-actin. Membranes were washed and incubated with IRDye Secondary Antibodies (1:25,000) for 1 hour at room temperature. A standard protocol was then followed for signal detection and band quantification, using the Odyssey® Infrared Imaging System and software (LI-COR Biosciences).

Figure 4A:
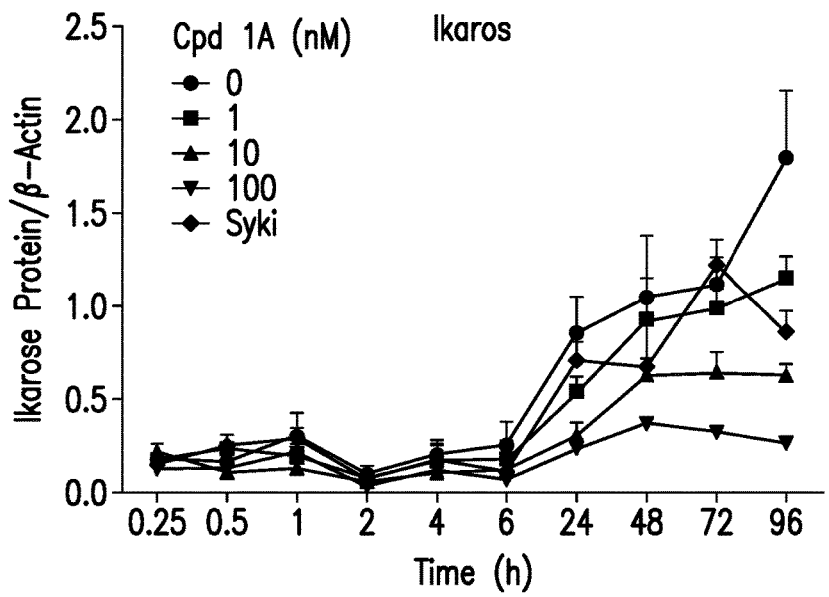
FIG. 4A and FIG. 4B depict effects of B cell stimulation and Compound 1A on Ikaros and Aiolos protein levels over time.
Figure 4B:
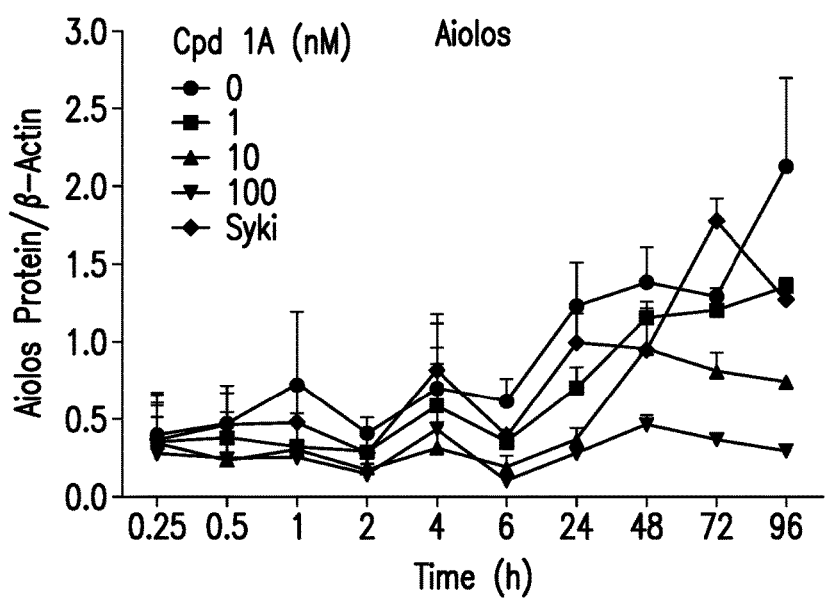

Effect of Compound 1A on Aiolos and Ikaros protein levels during CD19+ B Cell Culture are depicted in FIG. 4A and FIG. 4B, respectively. Ikaros and Aiolos were measured by western blot.

Whole blood samples from patients identified with SLE were obtained from Sanguine Biosciences; Inc. the blood was diluted with sterile Dulbecco's phosphate buffered saline solution (DPBS) and placed into three 50-mL conical tubes. Approximately 12 mL of Ficoll-Plaque was gently under-layered in each tube and the tubes were centrifuged at 1000 g for 35 minutes without brake. The interface containing mononuclear cells was collected and transferred into two 50-mL conical tubes and the volume in each conical tube was adjusted to 50 mL using DPBS. The mononuclear cells were washed with DPBS to remove Ficoll and platelets and after three washes the cell pellet was resuspended in 40 mL of B cell medium (Iscove's modified Dulbecco's medium +10% fetal bovine serum (FBS), 1% penicillin/streptomycin P/S, and 2 mM of L-Glutamine) to obtain a viability and cell count using trypan blue dye exclusion method. PBMCs were activated using the B cell differentiation cocktail described for FIG. 4A and FIG. 4B above. Cell culture supernatants were harvested and analyzed for autoantibodies using an Anti-double stranded DNA antibody ELISA kit (Orgentec ORG 604S) and an Anti-Cardiolipin/Phospholipid ELISA kit (Orgentec ORG-529).

Figure 5A:
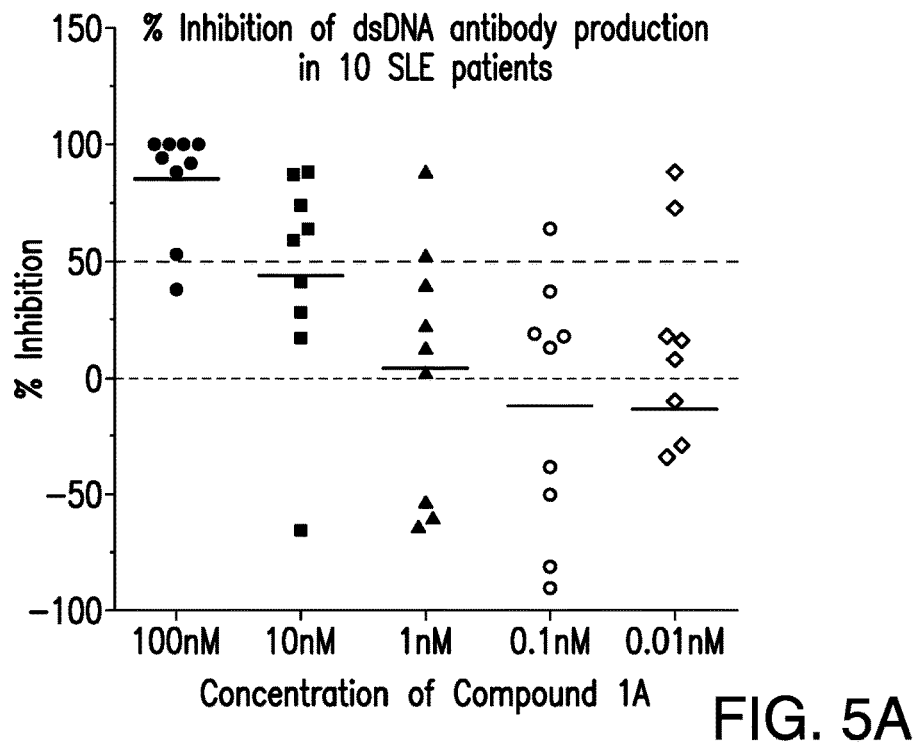
FIG. 5A and FIG. 5B depict that Compound 1A inhibited SLE autoantibody production in vitro.
Figure 5B:
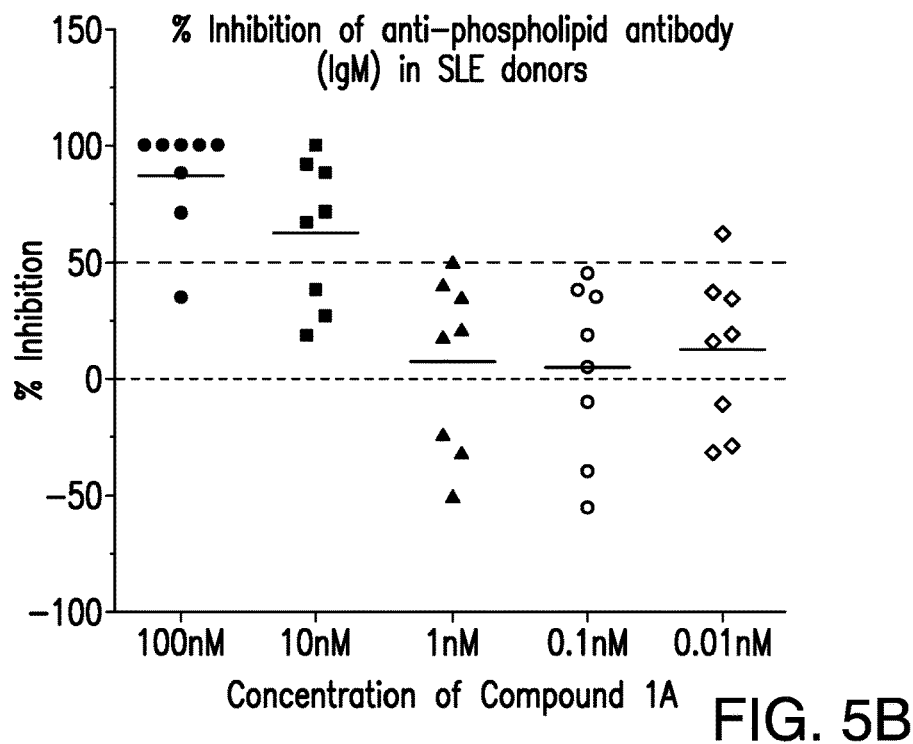

Compound 1A also inhibited SLE autoantibody production in vitro (FIG. 5A and FIG. 5B). In cultures of SLE PBMC, Compound 1A inhibited production of anti-dsDNA autoantibodies (N=9) and anti-phospholipid autoantibodies (N=8) with an IC50 of approximately 10 nM.

6.5 Example 5: Effects of Compound 1a in Healthy Volunteers

Healthy volunteers were administered placebo (n=10) or Compound 1A at doses of 0.03 mg, 0.1 mg, 0.3 mg, 1 mg, or 2 mg (N=6 each). Blood samples were drawn prior to dosing, or 3 hr, 12 hr, and 24 hr after dosing. Blood samples were lysed and fixed immediately by mixing 1 volume of blood with 20 volumes of 1× Lyse/Fix buffer (BD Biosciences, cat #558049) and mixing thoroughly by inverting the tube several times. This sample mix was incubated in a 37° C. water bath for 10 minutes., and the cells were pelleted by centrifugation at 800×g for 5 minutes to remove the supernatant by aspiration. The cells were washed twice with 2 mL of cold phosphate buffer saline (PBs), then permeabilized by adding 2 mL of cold BD Cytofix/cytoperm buffer and incubated on ice for 15 minutes. The cells were centrifuged than washed twice with BD perm/wash buffer, then resuspended in 40 ul of BD perm/wash buffer. Cells were stained with anti-CD3 or anti-CD19 antibody, and 20 ul of anti-Aiolos Ab (Santa Cruz Santa Cruz, rabbit polyclonal IgG, cat #sc-101982 at 1:200 dilution with staining buffer), or 20 uL of appropriate isotype controls to cells. Cells were mixed thoroughly and incubated at room temperature for 30 minutes in the dark, washed once with BD perm/wash buffer, then resuspended in 80 ul of BD perm/wash buffer, and 20 uL of secondary antibody was added before analysis on a flow cytometer.

The results demonstrate that Compound 1A reduced Aiolos expression in B cells (FIG. 6A) and in T cells (FIG. 6B) at 0.3 mg, 1 mg, and 2 mg cohorts in healthy volunteers. FIG. 6A shows that, following administration of single doses of Compound 1A to healthy volunteers, there was a treatment-related decrease in B cell intracellular Aiolos. At 12 hours postdose, the 1- and 2-mg groups had percent of baseline values of 28.2% and 25.0%, respectively. At 24 hours postdose, the 0.3-mg group had percent of baseline values of 24.8%. FIG. 6B shows that, following administration of single doses of Compound 1A to healthy volunteers, there was a treatment-related decrease in T cell intracellular Aiolos. At 12 hours postdose, the 1- and 2-mg groups had percent of baseline values of 22.3% and 26.1%, respectively; and at 24 hours postdose, the 0.3-mg group had percent of baseline values of 0%.

Compound 1A also dose-dependently reduced peripheral blood B cell counts (FIG. 7A) in healthy volunteers. There was a dose-related decrease in the maximum response in absolute CD19+ cells between 0.3 and 2 mg Compound 1A, with mean percent of baseline values of 73.5% on Day 3 for 0.3 mg, 67.3% on Day 2 for 1 mg, and 51.3% on Day 3 for 2 mg. Absolute B cell counts in the peripheral blood were measured by flow cytometry with anti-CD19 antibody as described above.

Compound 1A also reduced peripheral blood T cell counts (FIG. 7B) in healthy volunteers. The results show that the T cell decrease is more modest than B cell decrease. On Day 2, the 0.3-mg group had a percent of baseline value of 84.1% and the 1-mg group had 79.4%. On Day 5, the 2-mg group had a percent of baseline value of 73.8%. Absolute T cell counts in the peripheral blood were measured by flow cytometry with anti-CD3 antibody as described above.

Whole blood was stimulated with anti-CD3 antibody and analyzed for IL-2 using the CD3 TruCulture system (Part number 782-001202) by Myriad Rules Based Medicine (Austin, Tex.). FIG. 8A shows that Compound 1A dosing in healthy volunteers increased IL-2 production (pg/mL) in anti-CD3-stimulated whole blood ex vivo. There was a dose-related increase in the maximum IL-2 in the 0.3-, 1-, and 2-mg groups, with mean percent of baseline values of 315%, 973%, and 915%, respectively, at 12 hours postdose on Day 1.

Whole blood was stimulated with lipopolysachharide and analyzed for IL-1β using the LPS TruCulture system (Part number 782-001087) by Myriad Rules Based Medicine (Austin, Tex.). FIG. 8B shows that Compound 1A dose-dependently decreased ex vivo IL-1β production in healthy volunteers at 0.3 mg, 1 mg, and 2 mg cohorts. For dose levels 0.3, 1, and 2 mg, there was a dose-related decrease in the maximum IL-1β response, with mean percent of baseline values of 42.2%, 21.8%, and 16.3%, respectively, at 12 hours postdose.

What is claimed is:

1. A method for identifying a subject having systemic lupus erythematosus (SLE) who is likely to be responsive to a treatment with a compound of formula I

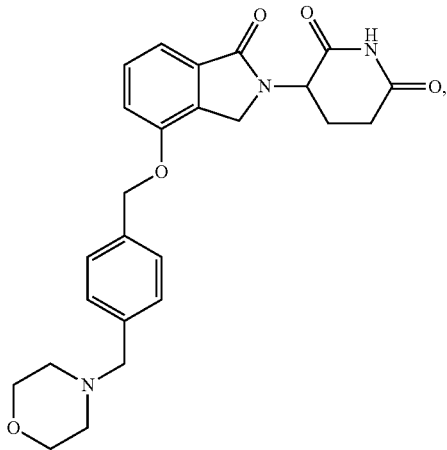

or a pharmaceutically acceptable salt, stereoisomer, tautomer or racemic mixture thereof, comprising:
- (a) determining the level of a biomarker in a first sample from the subject, wherein the biomarker is selected from the group consisting of CRBN, IKZF1 (Ikaros), and IKZF3 (Aiolos); and
- (b) comparing the level of the biomarker in the first sample to a reference level of the biomarker; wherein the subject is likely to be responsive to the treatment if the level of the biomarker in the first sample is higher than the reference level of the biomarker.

2. The method of claim 1, further comprising administering to the subject an effective amount of the compound.

3. The method of claim 1 or 2, wherein the reference is prepared by using a second sample obtained from a healthy subject not having SLE; and wherein the second sample is from the same source as the first sample.

4. The method of claim 1 or 2, wherein the biomarker is CRBN.

5. The method of claim 1 or 2, wherein the biomarker is IKZF1.

6. The method of claim 1 or 2, wherein the biomarker is IKZF3.

7. The method of claim 1 or 2, wherein the level of only one of the biomarkers is measured.

8. The method of claim 1 or 2, wherein the levels of two or more of the biomarkers are monitored simultaneously.

9. The method of claim 1 or 2, wherein the first sample is peripheral blood mononuclear cells (PBMC).

10. The method of claim 1 or 2, wherein the first sample is whole blood leukocyte.

11. The method of claim 10, wherein the whole blood leukocyte is CD19+ B cells, CD3+ T cells, CD14+ monocytes, or granulocytes.

12. The method of claim 1 or 2, wherein the levels of one or more of the biomarkers are measured by determining the mRNA levels of the biomarkers.

13. The method of claim 1 or 2, wherein the levels of one or more of the biomarkers are measured by determining the cDNA levels of the biomarkers.

14. The method of claim 1 or 2, wherein the levels of one or more of the biomarkers are measured by determining the protein levels of the biomarkers.

15. The method of claim 1 or 2, wherein the compound is (S)-3-(4-((4-(morpholinomethyl)benzyl)oxy)-1-oxoisoindolin-2-yl)piperidine-2,6-dione.

16. The method of claim 1 or 2, wherein the compound is (S)-3-(4-((4-(morpholinomethyl)benzyl)oxy)-1-oxoisoindolin-2-yl)piperidine-2,6-dione hydrochloride.

* * * * *